United States Patent
Nishii et al.

(10) Patent No.: US 11,988,666 B2
(45) Date of Patent: May 21, 2024

(54) LECTIN-BINDING SUBSTANCE MEASUREMENT METHOD, LECTIN-BINDING SUBSTANCE MEASUREMENT KIT, AND BLOCKED LABELED LECTIN FOR USE IN THESE

(71) Applicant: FUJIREBIO INC., Tokyo (JP)

(72) Inventors: Tomonori Nishii, Tokyo (JP); Kazunori Okada, Hachioji (JP); Naoki Ishikawa, Hachioji (JP); Kumiko Iida, Hachioji (JP); Shintaro Yagi, Hachioji (JP); Katsumi Aoyagi, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 17/639,391

(22) PCT Filed: Sep. 1, 2020

(86) PCT No.: PCT/JP2020/033137
§ 371 (c)(1),
(2) Date: Mar. 1, 2022

(87) PCT Pub. No.: WO2021/045061
PCT Pub. Date: Mar. 11, 2021

(65) Prior Publication Data
US 2022/0326245 A1    Oct. 13, 2022

(30) Foreign Application Priority Data
Sep. 2, 2019 (JP) .................................. 2019-159746

(51) Int. Cl.
*G01N 33/574* (2006.01)

(52) U.S. Cl.
CPC . *G01N 33/57484* (2013.01); *G01N 2333/471* (2013.01); *G01N 2333/4724* (2013.01)

(58) Field of Classification Search
CPC ................................................ G01N 33/57484
See application file for complete search history.

(56) References Cited

U.S. PATENT DOCUMENTS

| 4,692,330 | A  | * | 9/1987 | Ryohei | ............. | G01N 33/54393 |
|---|---|---|---|---|---|---|
|   |   |   |   |   |   | 436/538 |
| 9,005,910 | B2 | * | 4/2015 | Ohiro | ............... | G01N 33/54353 |
|   |   |   |   |   |   | 435/7.5 |

(Continued)

FOREIGN PATENT DOCUMENTS

| JP | S61-79164 A |   | 4/1986 |
|---|---|---|---|
| JP | 07083922 A | * | 3/1995 |

(Continued)

OTHER PUBLICATIONS

Bernard Van Eerdenbrugh et al., Molecular Weight Effects on the Miscibility Behavior of Dextran and Maltodextrin with Poly(vinylpyrrolidone), Pharm Res (2012) 29:2754-2765 (Year: 2012).*

(Continued)

*Primary Examiner* — Paul S Hyun
*Assistant Examiner* — Mickey Huang
(74) *Attorney, Agent, or Firm* — Oliff PLC

(57) ABSTRACT

A lectin-binding substance measurement method is a method for measuring a lectin-binding substance in a sample, and includes a measuring step of bringing a blocked labeled lectin including a water-soluble carrier made of a first water-soluble polymer and a labeling substance and a lectin immobilized on the water-soluble carrier into contact with the sample.

17 Claims, 1 Drawing Sheet

(56) References Cited

U.S. PATENT DOCUMENTS

| | | | |
|---|---|---|---|
| 2001/0005583 A1 | 6/2001 | Ohbayashi et al. | |
| 2004/0002146 A1 | 1/2004 | Ohbayashi et al. | |
| 2008/0153089 A1* | 6/2008 | Aoyagi | G01N 33/581 435/7.1 |
| 2013/0171740 A1* | 7/2013 | Sakakibara | G01N 33/54388 436/501 |
| 2013/0230897 A1 | 9/2013 | Ohiro et al. | |
| 2017/0122940 A1* | 5/2017 | Kaneko | G01N 33/54393 |

FOREIGN PATENT DOCUMENTS

| | | | | |
|---|---|---|---|---|
| JP | H07-083922 | A | | 3/1995 |
| JP | H07-325083 | A | | 12/1995 |
| JP | 2001-181299 | A | | 7/2001 |
| JP | 2018-04323 | A | | 1/2018 |
| JP | 2018004323 | A | * | 1/2018 |
| WO | 2006/070732 | A1 | | 7/2006 |
| WO | 2011/129357 | A1 | | 10/2011 |
| WO | 2013/021962 | A1 | | 2/2013 |
| WO | WO-2013021962 | A1 | * | 2/2013 ........... G01N 33/564 |
| WO | 2017/183711 | A1 | | 10/2017 |

OTHER PUBLICATIONS

Katsuya et al., WO2013021962A1 translated Description, 2013, Espacenet (Year: 2013).*

Kawabe et al., JP-07083922-A translated Description, 1995, JPO (Year: 1995).*

Nakada et al., JP-2018004323-A translated Description, 2018, JPO (Year: 2018).*

V. Čeřovský et al., Studies on lectins. XLIX. The use of glycosyl derivatives of dextran T-500 affinity electrophoresis of lectins (Abstract), 1980, Journal of Biochemical and Biophysical Methods, vol. 3, Issue 3, pp. 163-172 (Year: 1980).*

Pustylnikov et al., Targeting the C-type Lectins-Mediated Host-Pathogen Interactions with Dextran, 2014, J Pharm Pharm Sci (www.cspsCanada.org) 17(3) 371-392 (Year: 2014).*

Benzeval, I, Bowyer, A & Hubble, J 2012, 'The influence of degree-of-branching and molecular mass on theinteraction between dextran and Concanavalin A in hydrogel preparations intended for insulin release', European Journal of Pharmaceutics and Biopharmaceutics, vol. 80, No. 1, pp. 143-148 (Year: 2012).*

Singh et al., Dextran structural factors which affect binding to the lectin of *Streptococcus cricetus*, 1996, Carbohydrate Polymers, vol. 31, Issue 3, Nov. 1996, pp. 135-140 (Year: 1996).*

Mar. 8, 2022 International Preliminary Report on Patentability issued in International Application No. PCT/JP2020/033137.

Dec. 1, 2020 International Search Report issued in International Patent Application No. PCT/JP2020/033137.

Aug. 29, 2023 Extended European Search Report issued in European Patent Application No. 20859746.8.

* cited by examiner

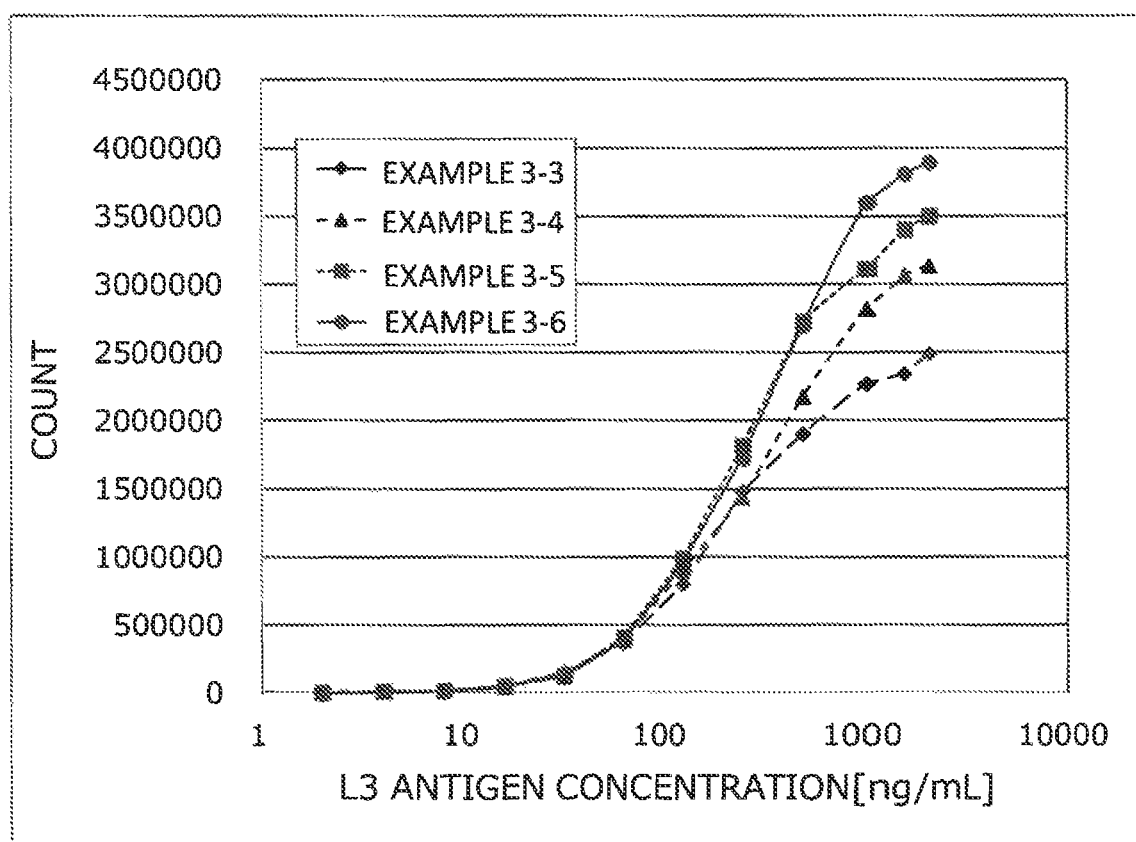

LECTIN-BINDING SUBSTANCE MEASUREMENT METHOD, LECTIN-BINDING SUBSTANCE MEASUREMENT KIT, AND BLOCKED LABELED LECTIN FOR USE IN THESE

TECHNICAL FIELD

The present invention relates to a lectin-binding substance measurement method, a lectin-binding substance measurement kit, and a blocked labeled lectin for use in these.

BACKGROUND ART

In recent years, as markers for monitoring malignant diseases such as tumor markers, methods for measuring glycans or substances having glycans such as glycoproteins, glycolipids, and free glycans have been actively studied. Among these, a measurement method using a lectin that binds to a glycan portion of a measurement target substance and a measurement method using a combination of the above measurement method and measurement using an antibody of the measurement target substance have been attracting attention from the viewpoint of the ability to measure not only a quantitative change in a measurement target substance but also a qualitative change due to a change in a glycan therein. As such a measurement target substance (lectin-binding substance) that can be measured by using a lectin, for example, α-fetoprotein L3 (AFP-L3) having a glycan to which fucose is added (core fucose structure) is known to be a marker highly specific to hepatocellular carcinoma among α-fetoproteins (AFP), which are carcinoembryonic glycoproteins expressed in hepatitis, hepatic cirrhosis, hepatocellular carcinoma, and so on. Currently, "μTASWako AFP-L3", which is a combination of an antibody that binds to an AFP portion and a lectin (lens culinaris agglutinin (LCA)) that binds to a core fucose structure, is manufactured and sold as a reagent for detecting an AFP-L3 fraction by FUJIFILM Wako Pure Chemical Corporation. For this reagent, the LBA method (Liquid-phase Binding Assay) is used in which an immune complex formed after an antigen-antibody reaction is separated and measured in a liquid phase by an ion exchange column or electrophoresis. However, it is necessary to use a dedicated machine or the like with low versatility designed for carrying out the above method, and therefore there is a problem that the measurement cost is high.

As another method for measuring the above lectin-binding substance, for example, International Publication No. WO2017/183711 (PTL 1) describes a method for capturing lectin-target molecules (lectin-binding substance), the method including binding a lectin to the lectin-target molecules in the presence of a lectin-reactive glycan-containing entity.

In addition, in immunological measurement methods using a complex composed of a probe such as an antibody and a labeling substance such as an enzyme, various studies have been conducted for the purpose of enhancing the sensitivity. For example, as the above complex, International Publication No. WO2006/070732 (PLT 2) describes a blocked enzyme-probe complex in which two or more molecules as a carrier having a molecular weight of 20,000 to 4,000,000 are linked via an enzyme and a probe molecule is conjugated to the complex in which the carrier is bound to the enzyme, and Japanese Unexamined Patent Application Publication No. 2001-181299 (PLT 3) describes an enzyme-protein complex in which two or more molecules of an enzyme are conjugated to a carrier and a protein with a specific binding potency to other substance(s) is conjugated to at least one molecule of the two or more molecules of the enzyme. Moreover, for example, as measurement conditions, Japanese Unexamined Patent Application Publication Nos. 2018-4323 (PLT 4) and Sho 61-79164 (PLT 5) describe the coexistence of an activator such as dextran in an immunochemical reaction.

CITATION LIST

Patent Literature

[PTL 1] International Publication No. WO2017/183711
[PTL 2] International Publication No. WO2006/070732
[PTL 3] Japanese Unexamined Patent Application Publication No. 2001-181299
[PTL 4] Japanese Unexamined Patent Application Publication No. 2018-4323
[PTL 5] Japanese Unexamined Patent Application Publication No. Sho 61-79164

SUMMARY OF INVENTION

Technical Problem

However, a simple method for measuring a lectin-binding substance using a lectin has not yet been fully studied. In addition, the method for measuring a lectin-binding substance has a problem that simple use of a lectin has difficulty in achieving measurement with high sensitivity by the CLEIA method (chemiluminescent enzyme immunoassay) or the like because the affinity between the lectin and glycans is weak as compared with an antigen-antibody reaction. Further, in the measurement method using a lectin, the lectin non-specifically binds to a substance other than the target substance (for example, a lectin-recognizing glycan bound to a protein or the like other than the target), and therefore generates high background to exhibit low specificity, which also poses a problem that measurement with high sensitivity is difficult.

The present invention has been made in consideration of the above problems, and has an object to provide a lectin-binding substance measurement method and a lectin-binding substance measurement kit, which are capable of measuring a lectin-binding substance in a sample with high sensitivity in a simple procedure, and provide a blocked labeled lectin for use in these.

Solution to Problem

The present inventors have completed the present invention by finding out that, in measurement of a lectin-binding substance in a sample, use of a complex (blocked labeled lectin) including a water-soluble carrier made of a water-soluble polymer and a labeling substance and a lectin immobilized on the water-soluble carrier leads to sufficient improvement of the sensitivity of the measurement of the lectin-binding substance only by performing a simple manipulation including bringing the complex into contact with the sample.

The aspects of the present invention obtained from such findings are as follows.

(1) A lectin-binding substance measurement method for measuring a lectin-binding substance in a sample, including a measuring step of bringing a blocked labeled lectin including a water-soluble carrier made of a first water-soluble polymer and a labeling substance and a lectin immobilized on the water-soluble carrier into contact with the sample.

(2) The lectin-binding substance measurement method according to (1), in which the measuring step is carried out in the presence of a second water-soluble polymer.

(3) The lectin-binding substance measurement method according to (1) or (2), in which the blocked labeled lectin is a combination of a high molecular weight blocked labeled lectin in which the first water-soluble polymer has a weight average molecular weight of 200,000 or more and a low molecular weight blocked labeled lectin in which the first water-soluble polymer has a weight average molecular weight of less than 100,000.

(4) The lectin-binding substance measurement method according to any one of (1) to (3), in which the measuring step further includes a step of bringing a labeled lectin including a labeling substance and a lectin into contact with the sample.

(5) A blocked labeled lectin for use in the lectin-binding substance measurement method according to any one of (1) to (4), including: a water-soluble carrier made of a first water-soluble polymer; and a labeling substance and a lectin immobilized on the water-soluble carrier.

(6) A lectin-binding substance measurement kit for measuring a lectin-binding substance in a sample, including the blocked labeled lectin according to (5).

(7) The lectin-binding substance measurement kit according to (6), in which the blocked labeled lectin is a combination of a high molecular weight blocked labeled lectin in which the first water-soluble polymer has a weight average molecular weight of 200,000 or more and a low molecular weight blocked labeled lectin in which the first water-soluble polymer has a weight average molecular weight of less than 100,000.

(8) The lectin-binding substance measurement kit according to (6) or (7), further including a second water-soluble polymer.

(9) The lectin-binding substance measurement kit according to any one of (6) to (8), further including a labeled lectin including a labeling substance and a lectin.

Although the reason why the above object is achieved by the configuration of the present invention is not exactly clear, the present inventors presume as follows. Specifically, in the blocked labeled lectin for use in the lectin-binding substance measurement of the present invention, the lectin that binds to the lectin-binding substance and the labeling substance are immobilized on the water-soluble carrier made of the water-soluble polymer, so that a complex is formed by a series of multiple molecules of the lectin immobilized on the polymeric water-soluble carrier. When this complex comes into contact with a lectin-binding substance in a sample, these multiple molecules of the lectin bind to lectin-binding glycan structures of the lectin-binding substance, which is the target substance. Therefore, the present inventors presume that, even though the affinity of the lectin and each of the lectin-binding glycan structures at a binding point is weak, the single complex generates multiple binding points to thereby improve the affinity of the complex as a whole, and enables the measurement of the lectin-binding substance with high sensitivity.

Advantageous Effects of Invention

According to the present invention, it is possible to provide a lectin-binding substance measurement method and a lectin-binding substance measurement kit, which are capable of measuring a lectin-binding substance in a sample with high sensitivity in a simple procedure, and provide a blocked labeled lectin for use in these.

BRIEF DESCRIPTION OF DRAWINGS

FIG. 1 shows a curve expressing a relation between a count and an L3 antigen concentration in each of Examples 3-3 to 3-6.

DESCRIPTION OF EMBODIMENTS

Hereinafter, the present invention will be described in detail according to preferred embodiments thereof.

A lectin-binding substance measurement method of the present invention is a method for measuring a lectin-binding substance in a sample, the method including a measuring step of bringing a blocked labeled lectin including a water-soluble carrier made of a first water-soluble polymer and a labeling substance and a lectin immobilized on the water-soluble carrier into contact with the sample. In addition, a lectin-binding substance measurement kit of the present invention is a kit for measuring a lectin-binding substance in a sample, the kit including the blocked labeled lectin. Further, a blocked labeled lectin of the present invention is the aforementioned blocked labeled lectin for use in the lectin-binding substance measurement method and the lectin-binding substance measurement kit of the present invention described above.

[Sample]

A sample for use in the lectin-binding substance measurement method of the present invention is not particularly limited as long as it is a sample in which a lectin-binding substance can exist. In general, there are samples collected from a subject (preferably human), such as a diagnostic subject, for which a target lectin-binding substance is to be measured, the samples including: blood samples such as serum, plasma, and whole blood; urine; stool; oral mucosa; pharyngeal mucosa; intestinal mucosa; various kinds of biopsy samples; and so on. A preferable sample according to the present invention is an aqueous sample, and is serum or plasma. These samples may be diluted on an as-needed basis.

[Lectin-Binding Substance]

In the present invention, a "lectin-binding substance" refers to a glycan capable of binding to a lectin (a glycan having a lectin-binding glycan structure) or a substance having the glycan. More specifically, such lectin-binding substances include glycoproteins having a glycan capable of binding to a lectin, glycolipids having the glycan, and carbohydrates containing the glycan.

The lectin is a protein that recognizes a specific glycan structure and exhibits binding activity. As lectins, there are known, for example, lectins derived from animals (for example, vertebrates and invertebrates), plants (for example, leguminosae and poaceae), fungi (for example, mushrooms and rice malt). The lectins can be classified into fucose-specific lectins having an affinity for fucose, galectins having an affinity for galactose, sialic acid-reactive lectins, and so on depending on a glycan structure for which a lectin has an affinity. More specific examples of the lectins include anguilla anguilla agglutinin (AAA), aleuria aurantia lectin (AAL), agaricus blazei lectin (ABL), agrocybe cylindracea galectin (ACG), amaranthus caudatus lectin (ACL), *Aspergillus oryzae* lectin (AOL), *Arum maculatum* lectin (AML), *Allium sativum* lectin (ASL), banana lectin (BanLec), *Bur-*

*kholderia cepacian* lectin (BC2L), bauhinia purpurea lectin (BPL), colchicum autumnale lectin (CA), caragana arborescens agglutinin (CAA), calystegia sepium lectin (Calsepa), coprinopsis cinerea lectin (CGL2), *Cicer arietinum* agglutinin (CPA), cytisus sscoparius lectin (CSA), canavalia ensiformis lectin (Concanavalin A, ConA), dolichos biflorus agglutinin (DBA), dictyostelium discoideum lectin (Discoidin I), dictyostelium discoideum lectin (Discoidin II), datura stramonium lectin (DSL), sambucus nigra agglutinin (SNA), erythrina cristagalli lectin (ECL), euonymus europaeus lectin (EEL), *Escherichia coli*-derived cilia adhering substance F17G variant a (*Escherichia coli* lectin, F17AG), *Galanthus nivalis* lectin (GNL), griffonia simplicufolia lectin I, GSL I), griffonia simplicufolia lectin II (GSL II), homarus americanus lectin (HMA), helix pomatia agglutinin (HPA), hippeastrum hybrid lectin (HHL), iris hybrid, IRA), jack fruit lectin (Jacalin), Laburnum anagyroides lectin (LAL), Lima bean agglutinin (LBA), lens culinaris agglutinin (LCA), lotus tetragonolobus lectin (LTL), *Lycopersicon esculentum* lectin (LEL), *Maackia amurensis* leukoagglutinin lectin (*Maackia amurensis* lectin I, MAM), *Maackia amurensis* agglutinin lectin (*Maackia amurensis* lectin II, MAA), marasmius oreades agglutinin (MOA), maclura pomifera lectin (MPL), narcissus pseudonarcissus lectin (NPL), *Oryza sativa* lectin (Orysata), *Pseudomonas aeruginosa* lectin I (PA-IL), *Pseudomonas aeruginosa* lectin II (PA-IIL), phlebodium aureum lectin (PAL), *Phaseolus vulgaris* agglutinin-E, -L, -P (PHA-E,-L,-P), peanut agglutinin (PNA), pholiota squarrosa lectin (PhoSL), pleurocybella porrigens lectin (PPL), *Pisum sativum* agglutinin (PSA), polyporus squamosus lectin 1a (PSL 1a), psophocarpus tetragonolobus lectin I (PTL I), psophocarpus tetragonolobus lectin II (PTL II), pokeweed mitogen (PWM), *Ricinus communis* agglutinin I (RCA I), *Ricinus communis* agglutinin II (RCA II), robinia pseudoacacia agglutinin (RPA), ralstonia solanacearum-Fuc lectin (RS-Fuc), sambucus sieboldiana agglutinin (SAMB), soybean agglutinin (SBA), salvia horminum agglutinin (SHA), *Sophora japonica* agglutinin (SJA), salvia sclarea agglutinin (SSA), *Solanum tuberosum* lectin (STL), tulip lectin (TL), *Urtica dioica* agglutinin (UDA), ulex europaeus agglutinin I (UEA I), ulex europaeus agglutinin II (UEA II), vigna radiata agglutinin (VRA), vicia villosa lectin (VVL), wisteria floribunda agglutinin (WFA), wheat germ agglutinin (WGA), and so on.

The lectin-binding substance according to the present invention is not particularly limited, but is preferably a glycoprotein or glycolipid for use as a marker for monitoring a malignant disease such as a tumor marker, and more preferably a glycoprotein having a glycan capable of binding to the lectin. As the glycoprotein, there are glycoproteins derived from mammalian, birds, reptiles, amphibians, fishes, plants, insects, microbes, or viruses. More specifically, examples of the glycoprotein include α-fetoprotein (such as AFP-L3), basic fetoprotein (BFP), CA125, CA15-3, CA19-9, CA242, CA50, CA72.4, SPan-1, DUPAN-2, carcinoembryonic antigen (CEA), c-erB-2, cytokeratin 19 fragment (CYFRA), KL-6, elastase I, topcoat antigen, ganglioside fucosylated GM1 (Fuc-GM1), kallikrein-8, matriptase, immunity suppressive acidic protein, nerve cell adhesion factor (NCAM), NCC-ST-439, nerve-specific enolase (NSE), prostatic acidic phosphatase (PAP), protein induced by vitamin K absence or antagonist II (PIVKA-II), tissue polypeptide antigen, squamous cell carcinoma-related antigen (SCC), prostate-specific antigen (PSA), sialyl Lex-i antigen (SLX), sialyl Tn antigen (STN), tissue polypeptide antigen (TPA), γGTP, various immunoglobulins, lacto-series carbohydrate antigen, ganglioside, transferrin, haptoglobin, hemopexin, thyroglobulin, human chorionic gonadotropin (hCG), carcinoembryonic antigen-related cell adhesion molecule 1 (CEACAM1), cytoskeleton associated protein 4 (CKAP4), virus particles and virus-derived proteins, glypican, cadoherin, integrin, various membrane proteins, various extracellular matrix constituent proteins, various enzymes, and various carbohydrate antigens. The glycoprotein may be one kind of these alone or include two or more kinds of these. From the viewpoint of being more suitable for a method for assisting diagnosis specific to a malignant disease, the lectin-binding substance according to the present invention is preferably at least one kind selected from the group consisting of glycoproteins having a glycan capable of binding to a fucose-specific lectin among the above glycoproteins, is more preferably at least one kind selected from the group consisting of AFP-L3 and PSA (prostate-specific antigen), and is further preferably any one kind of these. Here, it is preferable to exclude antibodies each of which specifically recognizes a lectin from the lectin-binding substance according to the present invention.

[Blocked Labeled Lectin]

In the present invention, a "blocked labeled lectin" is a complex including a water-soluble carrier made of a water-soluble polymer and a labeling substance and a lectin immobilized on the water-soluble carrier and is a conjugate in which the water-soluble carrier, the labeling substance, and the lectin bind to each other directly or indirectly. The blocked labeled lectin of the present invention only has to be such that the labeling substance and the lectin are carried on the water-soluble carrier. The labeling substance and the lectin may bind to the water-soluble carrier independently of each other, any one of the water-soluble carrier, the labeling substance, and the lectin may bind to the other two, the lectin may bind to the water-soluble carrier via the labeling substance, or the labeling substance may bind to the water-soluble carrier via the lectin.

(Water-Soluble Carrier)

The water-soluble carrier included in the blocked labeled lectin of the present invention mainly functions as a carrier that carries the labeling substance and the lectin, and is made of a water-soluble polymer. The water-soluble polymer (hereinafter referred to as a "first water-soluble polymer") constituting the water-soluble carrier according to the present invention is not particularly limited as long as it is a water-soluble polymer capable of immobilizing and carrying the labeling substance and the lectin. In the present invention, the "water-soluble polymer" refers to a polymeric compound in which the solubility in water under normal temperature and normal pressure is more than 0.01 g/mL, is preferably 0.05 g/mL or more, and is more preferably 0.1 g/mL or more.

The first water-soluble polymer according to the present invention has a weight average molecular weight (a polystyrene-equivalent weight average molecular weight measured by gel permeation chromatography (GPC); the same applies below) of preferably 6,000 to 4,000,000 and more preferably 20,000 to 1,000,000 from the viewpoints of the measurement sensitivity and water-solubility. Furthermore, from the viewpoint that there is a tendency to enable a lectin-binding substance, that is, a measurement target substance, to be measured with higher sensitivity even when the concentration of the lectin-binding substance is low, the first water-soluble polymer preferably has a high molecular weight, and has a weight average molecular weight of preferably 20,000 to 1,000,000 and more preferably 50,000 to 700,000.

Moreover, the blocked labeled lectin of the present invention is also preferably a combination of a high molecular weight blocked labeled lectin in which the first water-soluble polymer has a weight average molecular weight of 200,000 or more and a low molecular weight blocked labeled lectin in which the first water-soluble polymer has a weight average molecular weight of less than 100,000 (more preferably 100,000 or less) and is more preferably a combination of a high molecular weight blocked labeled lectin in which the first water-soluble polymer has a weight average molecular weight of 200,000 to 700,000 (further preferably 250,000 to 500,000) and a low molecular weight blocked labeled lectin in which the first water-soluble polymer has a weight average molecular weight of 20,000 to 100,000 (further preferably 50,000 to 70,000). When the high molecular weight blocked labeled lectin and the low molecular weight blocked labeled lectin are combined, a measurable concentration range of a lectin-binding substance, which is a measurement target substance, tends to be widen more. The present inventors presume that this is because the low molecular weight blocked labeled lectin is incorporated into the high molecular weight blocked labeled lectin, thereby increasing the density in the blocked labeled lectin.

In addition, in the case where the high molecular weight blocked labeled lectin and the low molecular weight blocked labeled lectin are combined as the blocked labeled lectin of the present invention, a mass ratio between them (the mass of the high molecular weight blocked labeled lectin:the mass of the low molecular weight blocked labeled lectin) is preferably 10:1 to 1:10, more preferably 5:1 to 1:5, and further preferably 3:1 to 1:3.

Moreover, as the blocked labeled lectin of the present invention, one blocked labeled lectin may contain, as the first water-soluble polymer, multiple kinds of water-soluble polymers different in the weight average molecular weight.

Examples of the first water-soluble polymer according to the present invention include: polysaccharides such as dextran, aminodextran, Ficoll (trade name), dextrin, agarose, purulan, various celluloses (for example, hemicellulose, lignin, and so on), chitin, and chitosan; β-galactosidase; thyroglobulin; hemocyanin; polylysine; polypeptide; DNA; and modified products of these (for example, diethylaminoethyl dextran, dextran sodium sulfate, and so on). The first water-soluble polymer may be one kind of these alone or a combination of two or more kinds of these. From the viewpoints that a large quantity is obtainable with low cost and chemical treatments such as addition of a functional group and a coupling reaction are relatively easy, the first water-soluble polymer according to the present invention is preferably at least one kind selected from the group consisting of polysaccharides and modified products thereof among the above, is more preferably at least one kind selected from the group consisting of dextran, aminodextran, and the modified products thereof, and is further preferably dextran.

(Labeling Substance)

The labeling substance included in the blocked labeled lectin of the present invention mainly functions as a label for the blocked labeled lectin, and any of labeling substances used in the known immunological measurements may be used without particular limitation.

Examples of the labeling substance according to the present invention include enzymes; luminescent substances such as acridinium derivatives; fluorescent substances such as europium; fluorescent proteins such as allophycocyanin (APC) and phycoerythrin (R-PE); radioactive substances such as $^{125}$I; low molecular weight labeling substances such as fluorescein isothiocyanate (FITC) and rhodamine isothiocyanate (RITC); gold particles; avidin; biotin; latex; dinitrophenyl (DNP); and digoxigenin (DIG). The labeling substance may be one kind of these alone or a combination of two or more kinds of these. When an enzyme is used as the labeling substance, for example, a color-developing substrate, a fluorescent substrate, a chemiluminescent substrate, or the like is added as a substrate, so that it is possible to conduct detection and quantification of any of various substances depending on the substrate. Examples of the enzyme include, but not limited to, horseradish peroxidase (HRP), alkaline phosphatase (ALP), β-galactosidase (β-gal), glucose oxidase, and luciferase.

(Lectin)

Examples of the lectin included in the blocked labeled lectin of the present invention include lectins listed in the above lectin-binding substance. The lectin is not particularly limited, can be selected depending on a kind of a lectin-binding substance, which is a measurement target substance, and may be one kind alone or a combination of two or more kinds. Among them, the lectin included in the blocked labeled lectin of the present invention is preferably at least one kind selected from the group consisting of lens culinaris agglutinin (LCA), *Maackia amurensis* lectin I (MAM), aleuria aurantia lectin (AAL), and wisteria floribunda agglutinin (WFA) and is more preferably one kind selected from these from the viewpoint that glycoprotein measurement based on cancer-specific glycoforms appearing on proteins is used to assist in the diagnosis of a malignant tumor.

(Structure and Production Method of Blocked Labeled Lectin)

In the blocked labeled lectin of the present invention, the content of the labeling substance is not particularly limited and can be adjusted as appropriate depending on a measurement mechanism or the like. In order to more improve the measurement sensitivity, however, the content of the labeling substance is preferably set such that the number of molecules of the labeling substance binding to one molecule of the first water-soluble polymer is as large as possible. For example, when the labeling substance is an enzyme, the mass of the labeling substance (in the case of a combination of two or more kinds of labeling substances, the total of them) with respect to 100 parts by mass of the first water-soluble polymer (in the case of a combination of two or more kinds of first water-soluble polymers, the total of them; the same applies below) is preferably 100 to 1,000 parts by mass, and more preferably 300 to 800 parts by mass.

In the blocked labeled lectin of the present invention, the content of the lectin is not particularly limited. In order to more improve the measurement sensitivity, however, the content of the lectin is preferably set such that the number of molecules of the lectin binding to one molecule of the first water-soluble polymer is as large as possible. For example, the mass of the lectin (in the case of a combination of two or more kinds of lectins, the total of them) with respect to 100 parts by mass of the first water-soluble polymer is preferably 100 to 2,000 parts by mass and more preferably 300 to 1,500 parts by mass.

As the blocked labeled lectin of the present invention, the weight average molecular weight per molecule of the blocked labeled lectin is preferably 1,000,000 to 10,000,000 and more preferably 1,500,000 to 5,000,000. When the weight average molecular weight is 1,000,000 or more, the measurement sensitivity tends to become higher. On the other hand, when the weight average molecular weight is 10,000,000 or less, flocculation or the like in an aqueous solution tends to be sufficiently inhibited.

The blocked labeled lectin of the present invention can be produced by immobilizing the labeling substance and the lectin on the water-soluble carrier. As such a production method, a conventionally known method or a method according to it may be used as appropriate, and the labeling substance and the lectin (hereinafter, collectively referred to as the "carried substance" in some cases) may be directly or indirectly immobilized on the water-soluble carrier.

As a method for directly immobilizing the carried substance on the water-soluble carrier, for example, there is a method in which active groups such as a carboxy group, an epoxy group, a tosyl group, an amino group, a hydroxy group, an isothiocyanate group, an isocyanate group, an azido group, an aldehyde group, a carbonate group, an allyl group, an aminooxy group, a maleimide group, a thiol group, and a pyridyl disulfide group are added to the carried substance and/or the first water-soluble polymer constituting the water-soluble carrier, or water-soluble polymers having these active groups are used as the carried substance and/or the water-soluble carrier, and the carried substance is immobilized on the water-soluble carrier by covalent bonds using these active groups. As the carried substance and the first water-soluble polymer to which the above active groups are added, commercially available ones may be used as they are, or the carried substance and the water-soluble polymer may be prepared by introducing the above active groups into the surfaces thereof under appropriate reaction conditions. As one example, the thiol group can be introduced by using a commercially available reagent such as, for example, S-acetylmercaptosuccinic anhydride or 2-iminothiolane hydrochloride. In addition, a maleimide group may be introduced to an amino group on the carried substance and/or the first water-soluble polymer constituting the water-soluble carrier by using a commercially available reagent such as, for example, N-(6-maleimide caproyloxy) succinimide or N-(4-maleimide butyryloxy) succinimide. A pyridyl disulfide group may be introduced by using a commercially available reagent such as, for example, N-succinimidyl 3-(2-pyridyldithio)propionate (SPDP), N-{6-[3-(2-pyridyldithio)propionamido]hexanoyloxy}sulfosuccinimide, or sodium salt (Sulfo-AC5-SPDP). Moreover, a thiol group may be introduced by introducing a pyridyl disulfide group and then reducing this to the thiol group.

As a method for indirectly immobilizing the carried substance on the water-soluble carrier, there is a method for immobilization via a linker such as, for example, polyhistidine, polyethylene glycol, oligopeptide containing cysteine and/or lysine, and a linker molecule having the above active group (for example, hydrazine salt, hydrazide, AMAS (N-α-maleimidoacet-oxysuccinimide ester), BMPS (N-β-maleimidopropyl-oxysuccinimide ester), GMBS (N-γ-maleimidobutyryl-oxysuccinimide ester), MBS (m-maleimidobenzoyl-N-hydroxysuccinimide ester), SMCC (succinimidyl 4-(N-maleimidomethyl)cyclohexane-1-carboxylate), EMCS (N-ε-malemidocaproyl-oxysuccinimide ester), SMPB (succinimidyl 4-(p-maleimidophenyl) butyrate), SMPH (Succinimidyl 6-((beta-maleimidopropionamido)hexanoate)), LC-SMCC (succinimidyl 4-(N-maleimidomethyl)cyclohexane-1-carboxy-(6-amidocaproate)), Sulfo-KMUS (N-κ-maleimidoundecanoyl-oxysulfosuccinimide ester), SIA (succinimidyl iodoacetate), SBAP (succinimidyl 3-(bromoacetamido)propionate), SIAB (succinimidyl (4-iodoacetyl)aminobenzoate), Sulfo-SANPAH (sulfosuccinimidyl 6-(4'-azido-2'-nitrophenylamino)hexanoate), SDA (succinimidyl 4,4'-azipentanoate), Sulfo-SDAD (sulfosuccinimidyl 2-((4,4'-azipentanamido)ethyl)-1,3'-dithiopropionate), EDC (1-ethyl-3-(3-dimethylaminopropyl)carbodiimide hydrochloride), NHS (N-hydroxysuccinimide), BMPH (N-β-maleimidopropionic acid hydrazide), EMCH (N-ε-maleimidocaproic acid hydrazide), MPBH (4-(4-N-maleimidophenyl) butyric acid hydrazide), KMUH (N-κ-maleimidoundecanoic acid hydrazide), PDPH (3-(2-pyridyldithio)propionyl hydrazide), PMPI (p-maleimidophenyl isocyanate), and SPB (succinimidyl-[4-(psoralen-8-yloxy)]-butyrate)), and the like. The selection and the size of the linker may be set as appropriate in consideration of the strength of binding to the carried substance, steric hindrance due to immobilization of the carried substance on the water-soluble carrier, and so on.

In the method for producing the blocked labeled lectin of the present invention, the labeling substance and the lectin may be immobilized on the water-soluble carrier at one time, or immobilized separately one by one. From the viewpoint of the ease of production and the ease of control of the amounts of the labeling substance and the lectin, it is preferable to immobilize one of the labeling substance and the lectin on the water-soluble carrier first, and then to immobilize the other thereon.

Moreover, the blocked labeled lectin of the present invention can be produced by immobilizing the labeling substance and the lectin on different water-soluble carriers respectively, and binding the labeling substance immobilized on one of the water-soluble carriers (blocked labeling substance) and the lectin immobilized on the other water-soluble carrier (blocked lectin) directly or via the above linker or the like.

Such a production method is not particularly limited. When the labeling substance is an enzyme and the first water-soluble polymer is polysaccharide or glycoprotein as will be described in Examples later, the first water-soluble polymer is first oxidized with an oxidizing agent such as sodium periodate to add an aldehyde group, is reacted with hydrazine hydrochloride, and then is reduced with a reducing agent such as dimethylamine borane (DMAB) to be hydrazinated. On the other hand, the enzyme is also oxidized with an oxidizing agent such as sodium periodate to add an aldehyde group to the glycan thereof. Next, the hydrazine residue and the aldehyde group added above are reacted to form a hydrazone bond, thereby obtaining a first water-soluble polymer-enzyme conjugate. The obtained first water-soluble polymer-enzyme conjugate is treated with a crosslinker having an N-hydroxysuccinimide and a maleimide group at terminals (for example, such as SM(PEG)$_4$ or SMCC) to introduce the maleimide group. On the other hand, the lectin is thiolated with a thiolation reagent to add a thiol group, or the lectin, if having a disulfide bond in the molecule, is reduced to obtain a thiol group. Finally, the maleimide group introduced in the first water-soluble polymer-enzyme conjugate and the thiol group added to the lectin are bound together, so that three substances, that is, the first water-soluble polymer (water-soluble carrier)-enzyme-lectin, can be covalently bonded. With this method, it is possible to obtain a blocked labeled lectin in which the lectin binds to two or more molecules of the first water-soluble polymer which bind to each other via the enzyme. The ratio of the first water-soluble polymer, the labeling substance, and the lectin provided for these reactions may be selected as appropriate so as to achieve the preferable ranges of the contents of them in the blocked labeled lectin described above.

<Lectin-Binding Substance Measurement Method>

A lectin-binding substance measurement method of the present invention includes a measuring step of bringing the blocked labeled lectin of the present invention into contact with the sample. In the present invention, "measurement" includes detection for confirming the presence or absence of a lectin-binding substance, as well as quantification or semi-quantification of the amount of the lectin-binding substance.

In the present invention, the measurement of the lectin-binding substance is performed by detecting a signal generated by the labeling substance and quantifying the detected signal as needed. The above-mentioned "signal" includes coloration (color development), reflected light, light emission, fluorescence, radiation by a radioisotope, and the like, and includes not only signals which can be checked with the naked eyes but also signals which can be checked by a measurement method/device depending on the type of the signal. According to the lectin-binding substance measurement method of the present invention, the measurement sensitivity is high and the intensity of the signal generated by the labeling substance is sufficiently high. For this reason, the measurement method can be carried out by using a general-purpose automatic immunoassay apparatus commercially available for the immunological measurement methods as it is.

In the lectin-binding substance measurement method of the present invention, it is preferable to provide a purified sample as the sample, especially in the case of a blood sample such as serum, plasma or whole blood, to the measuring step. In other words, the lectin-binding substance measurement method of the present invention preferably includes a purification treatment and the aforementioned measuring step. The purification treatment is not particularly limited, but the following purification treatment is preferable.

[Purification Treatment]

In the lectin-binding substance measurement method of the present invention, it is preferable to perform the following purification treatment on a sample before a lectin-binding substance is measured by using a lectin, the purification treatment including:

a capturing step of bringing a capture carrier including a water-insoluble carrier and a molecule immobilized on the water-insoluble carrier, the molecule being a molecule capable of capturing the lectin-binding substance, into contact with the sample to cause the capture carrier to capture the lectin-binding substance;

a washing step of removing contaminants unbound to the capture carrier; and a releasing step of releasing the lectin-binding substance from the capture carrier to obtain a prepared sample.

(Capture Carrier (Target Substance-Capture Molecule-Immobilized Carrier))

In the present invention, a "capture carrier" is a complex including a water-insoluble carrier and a molecule immobilized on the water-insoluble carrier, and is a conjugate in which the molecule is a molecule capable of capturing a lectin-binding substance and the water-insoluble carrier and the molecule bind to each other directly or indirectly.

(Target Substance-Capture Molecule)

In the present invention, a "molecule capable of capturing a lectin-binding substance" is a molecule capable of binding to a lectin-binding substance, and capable of capturing the lectin-binding substance as a target substance (hereinafter referred to as a "target substance-capture molecule" in some cases). The target substance-capture molecule is not particularly limited as long as it has an ability to bind to the lectin-binding substance, and may be any of antibodies, binding proteins (such as protein A, protein G, and protein L), receptor proteins, nucleic acids, and the like. The antibody may be an polyclonal antibody or a monoclonal antibody. Further, in the present invention, the "antibodies" include not only complete antibodies but also antibody fragments (for example, Fab, Fab', F(ab')$_2$, Fv, single chain antibody, diabody, and the like) and a low molecular weight antibody to which a variable region of the antibody is bound. In the purification treatment, it is particularly desirable to wash away glycan-containing components other than the target substance. Therefore, it is preferable to exclude any lectin having glycan binding property from the target substance-capture molecule.

In addition, in the capture carrier according to the present invention, the target substance-capture molecule used in the purification treatment may be a molecule that specifically binds only to a glycan portion which the lectin recognizes and binds to (for example, an antibody capable of recognizing and binding to the same site as the lectin does), or may be a molecule capable of recognizing and binding to a portion other than the glycan portion (for example, a protein portion of the glycoprotein or a lipid portion of the glycolipid) or a portion including the glycan portion as a part thereof in the lectin-binding substance. However, the target substance-capture molecule is preferably a molecule capable of recognizing and binding to a portion other than the glycan portion in the lectin-binding substance and is preferably, for example, an anti-protein antibody against the protein portion of the glycoprotein (for example, anti-AFP antibody or anti-PSA antibody). Therefore, the target substance-capture molecule may be a molecule capable of capturing not only a lectin-binding substance (for example, AFP-L3 or PSA (prostate-specific antigen)), but also a substance obtained by excluding, from the lectin-binding substance, the glycan portion which the lectin recognizes and binds to (for example, only a protein portion of AFP, AFP-L1, or PSA).

The target substance-capture molecule can be produced by employing and modifying a conventionally known production method, or a general commercially available one may be used as appropriate. For example, when a lectin-binding substance is AFP-L3, a commercially available anti-AFP monoclonal antibody or the like may be used as appropriate.

(Water-Insoluble Carrier)

The water-insoluble carrier included in the capture carrier mainly functions as a carrier that carries and immobilizes the target substance-capture molecule and is made of a water-insoluble substance. In the present invention, a "water-insoluble substance" refers to a substance insoluble in water under normal temperature and normal pressure (the solubility in water is 0.001 g/mL or less and is preferably 0.0001 g/mL or less; the same applies below).

As a material for such a water-insoluble carrier, any of materials generally used for immunological measurements can be used without particular limitation. An example thereof is at least one kind selected from the group consisting of high molecular polymers (such as polystyrene, (meth) acrylic acid ester, polymethylmethacrylate, polyimide, and nylon), gelatin, glass, latex, silica, metals (such as gold and platinum), and metal compounds (such as iron oxide, cobalt oxide, and nickel ferrite). In addition, the material for the water-insoluble carrier may be a composite material of some of these or a composite material of any of these substances and another substance, or may be, for example, an organic-inorganic composite material including at least one kind of organic polymer in the group consisting of the high molecular polymers, the gelatin, and the latex listed above, and at least one kind of metal compound in the group consisting of iron oxide (such as spinel ferrite), cobalt oxide, and nickel ferrite. Moreover, the water-insoluble carrier may be surface-modified with an active group such as a carboxy group, an epoxy group, a tosyl group, an amino group, a hydroxy group, an isothiocyanate group, an isocyanate group, an azido group, an aldehyde group, a carbonate group, an allyl group, an aminooxy group, a maleimide group, or a thiol group.

Further, in the present invention, the form of the water-insoluble carrier is not particularly limited, and may be in any of forms such as, for example, a plate, fibers, a membrane, and particles. From the viewpoint of reaction efficiency, the particles are preferable. From the viewpoint of automation and shortening of time, magnetic particles are more preferable. As such a water-insoluble carrier, a conventionally known one can be used as appropriate, or a commercially available one can also be used as appropriate.

(Structure and Production Method of Capture Carrier)

In the capture carrier, the content of the target substance-capture molecule is not particularly limited, and can be adjusted as appropriate depending on the ease of binding between the target substance-capture molecule and the lectin-binding substance or the like. For example, the mass of the target substance-capture molecule (in the case of a combination of two or more kinds of target substance-capture molecules, the total of them) with respect to 100 parts by mass of the water-insoluble carrier (preferably particles) (in the case of a combination of two or more kinds of water-insoluble carriers, the total of them) is preferably 0.1 to 10 parts by mass and more preferably 1 to 5 parts by mass.

The capture carrier can be produced by immobilizing the target substance-capture molecule on the water-insoluble carrier. As such a production method, a conventionally known method or a method according to it may be used as appropriate, and the target substance-capture molecule may be directly or indirectly immobilized on the water-insoluble carrier. In the case of direct immobilization, for example, the water-insoluble carrier and/or the target substance-capture molecule having active groups such as a carboxy group, an epoxy group, a tosyl group, an amino group, a hydroxy group, an isothiocyanate group, an isocyanate group, an azido group, an aldehyde group, a carbonate group, an allyl group, an aminooxy group, a maleimide group, and a thiol group are(is) used, or the above active groups are added to them as needed, and the target substance-capture molecule can be directly immobilized on the water-insoluble carrier by binding these active groups. In the case of indirect immobilization, for example, a linker that binds to the target substance-capture molecule is immobilized on the water-insoluble carrier and the target substance-capture molecule is bound to the linker, so that the target substance-capture molecule can be indirectly immobilized on the water-insoluble carrier. The linker is not particularly limited, and examples thereof include a secondary antibody capable of binding to the target substance-capture molecule, protein G, protein A, a photodegradable photocleavable linker, a linker molecule having the active group listed above (for example, hydrazine salt, hydrazide, AMAS, BMPS, GMBS, MBS, SMCC, EMCS, SMPB, SMPH, LC-SMCC, Sulfo-KMUS, SIA, SBAP, SIAB, Sulfo-SANPAH, SDA, Sulfo-SDAD, EDC, NHS, BMPH, EMCH, MPBH, KMUH, PDPH, PMPI, and SPB), and the like. Further, the target substance-capture molecule may be immobilized on the water-insoluble carrier by modifying the target substance-capture molecule in some way and immobilizing a substance that captures the modified portion of the target substance-capture molecule on the water-insoluble carrier. For example, a typical example of the above modified portion is biotin and a typical example of the substance that captures the modified portion is streptavidin. However, the modified portion and the substance are not limited to these. A ratio between the water-insoluble carrier and the target substance-capture molecule provided for these reactions can be selected as appropriate so as to achieve the preferable range of the ratio in the capture carrier described above. In addition, if necessary, blocking of the water-insoluble carrier may be performed by using an appropriate blocking agent (for example, such as bovine serum albumin or gelatin) for the purpose of preventing non-specific adsorption to the target substance-capture molecule and the water-insoluble carrier. Further, as such a capture carrier, for example, a commercially available carrier such as anti-AFP antibody-binding particles or anti-PSA antibody-binding particles may be used as appropriate.

(Capturing Step)

In the capturing step, the capture carrier is brought into contact with the sample and thereby is caused to capture the lectin-binding substance through binding between the lectin-binding substance and the target substance-capture molecule. A method for bringing the capture carrier into contact with the sample is not particularly limited, and a conventionally known method or a method according to it can be used as appropriate. For example, in the case where the water-insoluble carrier is a plate and the capture carrier is a target substance-capture molecule-immobilized plate, there is a method for injecting the sample into this plate. In the case where the water-insoluble carrier is particles and the capture carrier is target substance-capture molecule-immobilized particles, there is a method for adding the target substance-capture molecule-immobilized particles to the sample.

The sample may be diluted with a sample diluent and used. In the case where the capture carrier is the target substance-capture molecule-immobilized particles, the capture carrier may be suspended in a particle suspension medium (particle solution) and used. In addition, another buffer for reaction may be added to a reaction system of the capture carrier and the sample (for example, an antigen-antibody reaction system) as appropriate. These sample diluent, particle suspension medium, and buffer for reaction are not particularly limited, and, for example, may be each independently any of known buffers (such as sodium phosphate buffer, MES, Tris, CFB, MOPS, PIPES, HEPES, tricine buffer, bicine buffer, and glycine buffer). The particle suspension medium and the buffer for reaction may be each independently added with a stabilizing protein such as BSA, serum, or the like.

In the reaction between the capture carrier and the sample in the capturing step, the content (final concentration) of the capture carrier (in the case of a combination of two or more kinds of capture carriers, the total of them; the same applies below) in the reaction solution containing the capture carrier and the sample is not particularly limited. Although the content of the capture carrier is not particularly limited because it is appropriately adjusted according to the kind, concentration, purpose of the purification treatment, and the like of the sample, the content is, for example, preferably 0.01 to 1.5% by mass, more preferably 0.05 to 1% by mass, and further preferably 0.1 to 0.5% by mass from the viewpoint of efficiently recovering the substance captured by the target substance-capture molecule within a short period of time.

In addition, the conditions in the capturing step are not particularly limited and can be adjusted as appropriate. For example, the capturing step may be performed at room temperature to 45° C. or preferably 20° C. to 37° C., at a pH of about 6 to 9 or preferably a pH of 7 to 8, for about 5 seconds to 10 minutes or preferably about 30 seconds to 5 minutes. However, the conditions are not limited to these conditions.

(Washing Step)

In the washing step, a target substance (including at least a lectin-binding substance in the case where the sample contains the lectin-binding substance) bound to the capture carrier and other contaminants unbound to (not captured by) the capture carrier are separated from each other and the contaminants are removed. A method for removing the contaminants is not particularly limited, and a conventionally known method or a method according to it can be used as appropriate. For example, in the case where the water-insoluble carrier is a plate and the capture carrier is a target substance-capture molecule-immobilized plate, there is a method for removing a liquid phase (supernatant) from the plate after the aforementioned capturing step. In the case where the water-insoluble carrier is particles and the capture carrier is target substance-capture molecule-immobilized particles, there is a method for collecting the particles by centrifugation or magnetic collection after the aforementioned capturing step, and then removing the liquid phase (supernatant). In the washing step, thereafter, injection and removal of a washing liquid may be repeated as needed. Examples of the washing liquid include neutral (preferably a pH of 6 to 9) known buffers (such as sodium phosphate buffer, MES, Tris, CFB, MOPS, PIPES, HEPES, tricine buffer, bicine buffer, and glycine buffer), and the washing liquid may be added with a stabilizing protein such as BSA, a surfactant, or the like.

(Releasing Step)

In the releasing step, the lectin-binding substance bound to the capture carrier is released from the capture carrier to obtain a prepared sample containing the re-released lectin-binding substance as a sample for use in the measuring step. A method for releasing the lectin-binding substance from the capture carrier is not particularly limited, and may be a method for acidifying or alkalinizing the reaction system; a method for cleaving a photocleavable linker by light irradiation in the case where the photocleavable linker is used as the linker; a method using a surfactant; a method using a protein denaturing agent; a method for applying heat; a method using a combination of the above methods; or the like.

For example, in the case of acidifying the reaction system, there is a method for bringing an eluate preferably having a pH of 4 or less (more preferably, a pH of 3 to 1) into contact with the capture carrier to which the lectin-binding substance is bound. In the case of alkalinizing the reaction system, there is a method for bringing an eluate preferably having a pH of 9 or more (more preferably, a pH of 10 to 14) into contact with the capture carrier. The eluate is one containing an acidifying agent (for example, hydrochloric acid, sulfuric acid, acetic acid, or citric acid), an alkalizing agent (for example, sodium hydroxide, potassium hydroxide, or magnesium hydroxide), or the like. In these cases, after that, it is preferable to neutralize the reaction system by adding a neutralizing agent (for example, hydrochloric acid, sulfuric acid, acetic acid, citric acid, sodium hydroxide, potassium hydroxide, magnesium hydroxide, or a known buffer solution prepared to be alkaline or acidic) or the like to the eluate.

The other conditions in the releasing step are not particularly limited and can be adjusted as appropriate depending on the method. For example, the releasing step may be performed at room temperature to 37° C. or preferably 20° C. to 37° C. for about 5 seconds to 10 minutes or preferably about 30 seconds to 5 minutes. However, the conditions are not limited to these conditions.

[Measuring Step]

As a principle of the measurement method for measuring a lectin-binding substance of the present invention, any of the same principles as the sandwich method, the competitive method, the immunoturbidimetry method and the like in the immunological measurement methods can be employed. In the lectin-binding substance measurement method of the present invention, the quantification of the lectin-binding substance in the sample can be generally performed by employing a method in which a microplate, particles, or the like is used as a carrier, such as ELISA, digital ELISA, CLEIA (chemiluminescent enzyme immunoassay), CLIA (chemiluminescent immunoassay), ECLIA (electro chemiluminescent immunoassay), or RIA (radioimmunoassay), performing detection and quantification depending on a kind of the labeling substance, and comparing the obtained value with the measured value in a standard sample. On the other hand, from the viewpoint of detecting the lectin-binding substance more easily and quickly, for example, a method such as immunochromatography can be employed as the sandwich method.

As the lectin-binding substance measurement method of the present invention, a method preferable from the viewpoint that the method tends to enable construction of a detection system with higher sensitivity and higher specificity is the sandwich method which uses an antibody capable of capturing a lectin-binding substance and measures the lectin-binding substance by using any one of the antibody and a blocked labeled lectin as a trap and the other one as a detectable substance (label). As the sandwich method, there are a two-step forward sandwich method (a reaction between the trap and the lectin-binding substance in the sample, and a reaction between the lectin-binding substance bound to the trap and the detectable substance are performed sequentially), a reverse sandwich method (the detectable substance is reacted with the lectin-binding substance in the sample in advance, and the generated complex is reacted with the trap), and a one-step method (the reactions between the trap, the lectin-binding substance in the sample, and the detectable substance are performed concurrently in one step). Any of these methods may be employed.

More preferably, for example, the aforementioned forward sandwich method may be performed as follows. First, an antibody capable of capturing a lectin-binding substance is used as a trap (capture antibody), and a water-insoluble carrier on which the antibody is immobilized is brought into contact with and bound to the lectin-binding substance in the sample (primary reaction step). After that, the lectin-binding substance unbound to the capture antibody and contaminants are removed with an appropriate washing liquid (for example, a buffer solution or the like) as needed. Next, the blocked labeled lectin of the present invention as a detectable substance is brought into contact with and bound to the lectin-binding substance captured by the capture antibody (secondary reaction step). As a result of this reaction, an immune complex containing the capture antibody-the lectin-binding substance-the blocked labeled lectin is formed on the water-insoluble carrier. The detectable substance (blocked labeled lectin) unbound is washed away with a washing liquid, and then the labeling substance in the detectable substance is measured by a predetermined method. For example, when the labeling substance contained in the blocked labeled lectin is an enzyme, a color-developing substrate or a luminescent substrate specific to the enzyme is added, and a signal generated by a reaction of the enzyme with the substrate is measured.

As the "antibody capable of capturing a lectin-binding substance" for use in the aforementioned sandwich method, the same antibodies as listed above in the target substance-capture molecule can be used. From the viewpoint of further enhancing the measurement accuracy, the antibody capable of capturing a lectin-binding substance for use in the measuring step is not an antibody that specifically binds only to a glycan portion which the lectin recognizes and binds to (that is, an antibody that recognizes or physically covers and binds to the same site as the lectin does), or an antibody that recognizes and binds to a portion including the glycan portion as a part thereof, but is preferably an antibody that recognizes and binds to a portion other than the glycan portion (for example, a protein portion of the glycoprotein or a lipid portion of the glycolipid) in the lectin-binding substance. In addition, an antibody not having a glycan structure that the lectin recognizes, for example, such as Fab, Fab', or F(ab')$_2$ fragment is also preferable. Moreover, as the antibody capable of capturing a lectin-binding substance for use in the measuring step, a complete antibody may be used. However, it cannot be denied that the complete antibody having a glycan structure may cause a non-specific reaction with the lectin and increase the background. For this reason, it is more preferable to prepare antigen-binding fragments not having a glycan structure or destroy the glycans on the antibody in advance.

In addition, the "water-insoluble carrier" for use in the above sandwich method is not particularly limited as long as it is capable of immobilizing and carrying the antibody and is insoluble in water under normal temperature and normal pressure, and it is possible to use the same carriers as listed above as the water-insoluble carrier contained in the capture carrier in the purification treatment.

The "water-insoluble carrier on which the capture antibody is immobilized" for use in the above sandwich method can be produced in the same manner as in the method for immobilizing the target substance-capture molecule on the water-insoluble carrier in the purification treatment described above (the capture carrier production method).

As a method for the above contact in the lectin-binding substance measurement method of the present invention, a conventionally known method or a method according to it can be used as appropriate. For example, in the case where the water-insoluble carrier is a plate, there is a method for injecting the sample and the blocked labeled lectin into this plate. In the case where the water-insoluble carrier is particles, there is a method for mixing the particle solution, the sample, and a solution of the blocked labeled lectin with each other at one time or sequentially.

In the lectin-binding substance measurement method of the present invention, the content (final concentration) of the blocked labeled lectin (in the case of a combination of two or more kinds of blocked labeled lectins, the total of them; the same applies below) in a reaction solution containing the blocked labeled lectin and the lectin-binding substance in the measuring step, that is, in the reaction between the blocked labeled lectin and the lectin-binding substance is not particularly limited. Although the content of the blocked labeled lectin is not particularly limited because it may be adjusted as appropriate depending on the kind, concentration, and the like of the sample, the content is, for example, preferably 0.001 to 10 μg/mL, more preferably 0.01 to 5 μg/mL, and further preferably 0.1 to 1 μg/mL from the viewpoint that there is a possibility that the blocked labeled lectin, if used excessively, may generate a high background signal.

In the lectin-binding substance measurement method of the present invention, the other conditions in the measuring step are not particularly limited, and can be adjusted as appropriate. For example, the reaction between the blocked labeled lectin and the lectin-binding substance can be performed at room temperature to 37° C. or preferably 20° C. to 37° C., at a pH of 5.0 to 7.0 or preferably 5.5 to 6.5, for about 3 minutes to 120 minutes or preferably about 5 minutes to 10 minutes. However, the conditions are not limited to these conditions.

(Second Water-Soluble Polymer)

In the lectin-binding substance measurement method of the present invention, the measuring step, that is, the reaction between the blocked labeled lectin and the lectin-binding substance is preferably performed in the presence of a water-soluble polymer, in other words, under a condition where the water-soluble polymer, the blocked labeled lectin, and the sample (lectin-binding substance) coexist.

Unlike the first water-soluble polymer constituting the water-soluble carrier, the water-soluble polymer that preferably coexists with the blocked labeled lectin is a free water-soluble polymer (referred to as a second water-soluble polymer below) carrying none of the labeling substance and the lectin. In the lectin-binding substance measurement method of the present invention, the measurement sensitivity can be further improved when the second water-soluble polymer coexists in the measuring step.

The second water-soluble polymer may be any of the same polymers as listed as the first water-soluble polymer, and may be one kind of these alone or a combination of two or more kinds of these. The second water-soluble polymer may be the same kind of polymer as the first water-soluble polymer. Among these, the second water-soluble polymer is preferably at least one kind selected from the group consisting of polysaccharides and modified products thereof, more preferably at least one kind selected from the group consisting of dextran, aminodextran, and modified products thereof, and further preferably dextran from the viewpoint of the tendency to more improve the measurement sensitivity.

In addition, from the viewpoint of the tendency to more improve the measurement sensitivity, the weight average molecular weight of the second water-soluble polymer is preferably 500,000 to 5,000,000, more preferably 1,000,000 to 3,000,000, and further preferably 1,500,000 to 2,500,000.

In the case where the second water-soluble polymer coexists in the measuring step, the second water-soluble polymer may be added to the sample or a sample diluent in advance or added to a solution of the blocked labeled lectin in advance, or a solution of the second water-soluble polymer may be mixed with these. In this case, the amount of the second water-soluble polymer is not particularly limited, but the content of the second water-soluble polymer (in the case of a combination of two or more kinds of second water-soluble polymers, the total of them) in a reaction solution containing the sample, the blocked labeled lectin, and the second water-soluble polymer is preferably 0.01 to 10 w/v % and more preferably 0.5 to 3 w/v % (w/v %: weight/volume (g/mL) percent; the same applies below).

(Labeled Lectin)

In the lectin-binding substance measurement method of the present invention, the measuring step preferably includes a step of bringing a labeled lectin including a labeling substance and a lectin into contact with the sample, in other words, causing a reaction between the blocked labeled lectin and the lectin-binding substance and a reaction between the labeled lectin and the lectin-binding substance under the condition where the labeled lectin, the blocked labeled lectin, and the sample (lectin-binding substance) coexist. In the lectin-binding substance measurement method of the present invention, the coexistence of the labeled lectin in the measuring step makes it possible to further improve the measurement sensitivity. The present inventors presume that this is because the excessive existence of the lectin labeled by the reaction system more promotes the reaction between the lectin-binding substance and the blocked labeled lectin in the binding direction and the low-molecular labeled lectin can bind to the lectin-binding substance to which the high-molecular blocked labeled lectin cannot bind due to a steric hindrance.

In the present invention, the "labeled lectin" that preferably coexists with the blocked labeled lectin is a complex containing a labeling substance and a lectin and is a conjugate in which the labeling substance and the lectin bind to each other directly or indirectly. The labeled lectin is different from the blocked labeled lectin of the present invention in that the labeled lectin does not include the water-soluble carrier.

The labeling substance contained in the labeled lectin may be any of the same substances as listed as the labeling substance contained in the blocked labeled lectin of the present invention and may be one kind of these alone or a combination of two or more kinds of these. In addition, the labeling substance contained in the labeled lectin is preferably the same kind of substance as the labeling substance contained in the blocked labeled lectin.

The lectin contained in the labeled lectin may be any of the same lectins as listed as the lectin contained in the blocked labeled lectin of the present invention and may be one kind of these alone or a combination of two or more kinds of these. In addition, the lectin contained in the labeled lectin is preferably the same kind of lectin as the lectin contained in the blocked labeled lectin. Among these, the lectin contained in the labeled lectin is preferably at least one kind selected from the group consisting of lens culinaris agglutinin (LCA), *Maackia amurensis* lectin I (MAM), aleuria aurantia lectin (AAL), and wisteria floribunda agglutinin (WFA), and is more preferably any one kind of these.

The content ratio between the labeling substance and the lectin in the labeled lectin is not particularly limited, and can be adjusted as appropriate depending on a measurement mechanism and so on. However, for example, when the labeling substance is an enzyme, the content ratio between the labeling substance and the lectin (the mass of labeling substance: the mass of the lectin; in the case of a combination of two or more kinds of labeling substances and a combination of two or more kinds of lectins, the total of the labeling substances and the total of the lectins independently) is preferably 50:1 to 1:50, more preferably 10:1 to 1:10, and further preferably 5:1 to 1:5.

The labeled lectin can be produced by binding the labeling substance and the lectin to each other. As such a production method, a conventionally known method or a method according to it may be used as appropriate, and the labeling substance and the lectin may be directly or indirectly immobilized. As such a method, the same method as described as the method for producing the blocked labeled lectin of the present invention may be used. The ratio between the labeling substance and the lectin provided for these reactions may be selected as appropriate so as to achieve the preferable content ratio described above.

In the case where the labeled lectin coexists in the measuring step, the labeled lectin may be added to the sample or a sample diluent in advance or added to a solution of the blocked labeled lectin in advance, or a solution of the labeled lectin may be mixed with these. In this case, the amount of the labeled lectin is not particularly limited, but the content of the labeled lectin (in the case of a combination of two or more kinds of labeled lectins, the total of them) in a reaction solution containing the sample, the blocked labeled lectin, and the labeled lectin with respect to 100 parts by mass of the content of the blocked labeled lectin is preferably 1 to 1,000 parts by mass and more preferably 10 to 500 parts by mass.

In addition, in the measuring step of the lectin-binding substance measurement method of the present invention, it is also preferable that both of the labeled lectin and the second water-soluble polymer coexist, more specifically, the blocked labeled lectin and the lectin-binding substance react with each other and the labeled lectin and the lectin-binding substance react with each other under the condition where the blocked labeled lectin, the labeled lectin, the second water-soluble polymer, and the sample (lectin-binding substance) coexist.

(Free Lectin)

In the lectin-binding substance measurement method of the present invention, it is also preferable that the measuring step, specifically, the reaction between the blocked labeled lectin and the lectin-binding substance be performed in the presence of a free lectin, in other words, under the condition where the free lectin, the blocked labeled lectin, and the sample (lectin-binding substance) coexist. In this lectin-binding substance measurement method, the measuring step is also preferably performed under the condition where the second water-soluble polymer further coexists, in other words, where the blocked labeled lectin, the second water-soluble polymer, the free lectin, and the sample coexist. Moreover, the measuring step is also preferably performed under the condition where the labeled lectin coexists, in other words, where the blocked labeled lectin, the labeled lectin, the free lectin, and the sample coexist. Furthermore, the measuring step is also preferably performed under the condition where both of the second water-soluble polymer and the labeled lectin coexist, in other words, where the blocked labeled lectin, the second water-soluble polymer, the labeled lectin, the free lectin, and the sample coexist.

The free lectin preferably coexisting with the blocked labeled lectin is a free lectin not immobilized on the water-soluble carrier or the labeling substance unlike the lectin contained in the blocked labeled lectin and the lectin contained in the labeled lectin (hereinafter referred to as the "free lectin"). The lectin-binding substance measurement method using a lectin tends to have high background because the lectin non-specifically binds to substances other than the target substance (for example, a lectin recognizing glycan bound to a protein or the like other than the target). In contrast, in the lectin-binding substance measurement method of the present invention, the coexistence of the free lectin in the measuring step makes it possible to more suppress an increase in the background. The present inventors presume that one of the reasons for this is an appropriate masking effect produced by the free lectin. In addition, when the free lectin coexists, the reactivity of the blocked labeled lectin is improved in some cases. The present inventors presume that the reason for this is that the apparent valence of the blocked labeled lectin is increased when the polyvalent free lectin binds monovalently to the glycan structure of the blocked labeled lectin or that the parallel reactions of binding and unbinding between the blocked labeled lectin and the lectin-binding substance incline to the binding due to an increase in the local lectin concentration by the addition of the free lectin.

Such a free lectin may be any of the same lectins as listed above as the lectin, and may be one kind of these alone or a combination of two or more kinds of these. In addition, the free lectin may be the same kind as the lectin contained in the blocked labeled lectin. From the viewpoints of improving the sensitivity and suppressing the background, the free lectin is preferably at least one kind selected from the group consisting of lens culinaris agglutinin (LCA), *Maackia amurensis* lectin I (MAM), aleuria aurantia lectin (AAL), and wisteria floribunda agglutinin (WFA) among these, is more preferably at least one kind selected from the group consisting of lens culinaris agglutinin (LCA) and aleuria aurantia lectin (AAL), is further preferably any one kind of them, and is particularly preferably the same kind as the lectin contained in the blocked labeled lectin.

In the case where the free lectin coexists in the measuring step, the free lectin may be added to the sample or a sample diluent in advance or added to a solution of the blocked labeled lectin in advance, or a solution of the free lectin may be mixed with these. In this case, the amount of the free lectin is not particularly limited, but the content of the free lectin (in the case of a combination of two or more kinds of free lectins, the total of them) in a reaction solution containing the sample, the blocked labeled lectin (or the blocked labeled lectin and the labeled lectin), and the free lectin with respect to 100 parts by mass of the content of the blocked labeled lectin (or the total content of the blocked labeled lectin and the labeled lectin) is preferably 1 to 10,000 parts by mass and more preferably 10 to 5,000 parts by mass.

In the lectin-binding substance measurement method of the present invention, the sample diluted with a sample diluent or a prepared sample after the above purification treatment may be used as the sample. When the water-insoluble carrier in the sandwich method is particles, a suspension medium in which the particles are suspended may be used. Moreover, in the lectin-binding substance measurement method of the present invention, another buffer for reaction may be added as appropriate to the reaction system of the trap, the detectable substance, and the sample in the sandwich method. These sample diluent, particle suspension medium, and buffer for reaction may be the same ones as listed in the purification treatment described above, and each can be selected as appropriate without particular limitation.

<Lectin-Binding Substance Measurement Kit>

A lectin-binding substance measurement kit of the present invention includes at least the blocked labeled lectin of the present invention as a constituent reagent. In addition, the lectin-binding substance measurement kit preferably further includes at least one kind selected from the group consisting of the second water-soluble polymer, the labeled lectin, the free lectin, and the capture carrier. These may be each independently in a solid (powder) form or in a liquid form in which it is dissolved in a buffer solution. In the case of the liquid form, the concentrations of the blocked labeled lectin, the labeled lectin, and the capture carrier in the respective solutions (preparations) are not particularly limited. However, from the viewpoint that non-specific signals tend to increase due to excessive additions in some cases, the concentrations are each independently preferably 0.01 to 10 µg/mL, more preferably 0.1 to 5.0 µg/mL, and further preferably 0.5 to 3.0 µg/mL. In addition, the concentration of the second water-soluble polymer is preferably 0.01 to 10.0 w/v %, more preferably 0.1 to 5.0 w/v %, and further preferably 0.5 to 3.0 w/v %. Then, the concentration of the free lectin is preferably 1 µg/mL or more, more preferably 10 to 500 µg/mL, and further preferably 50 to 250 µg/mL.

The lectin-binding substance measurement kit of the present invention may further include constituent elements that should be provided for ordinary immunological measurements such as ELISA, CLEIA, or immunochromatography. For example, in the case where the sandwich method is employed as the principle of the measurement method, the lectin-binding substance measurement kit may further include at least one kind selected from the group consisting of a magnetic particle solution containing magnetic beads on which a trap is immobilized (or for immobilizing the trap), a plate on which the trap is immobilized (or for immobilizing the trap), a standard analyte reagent (each concentration), a control reagent, the sample diluent, the particle suspension medium, the buffer for reaction, the washing liquid, and a cartridge for dilution.

In the case where the labeling substance is an enzyme, the kit may further include a substrate, a reaction stop solution, and so on necessary for detection and quantification of the labeling substance. Further, the lectin-binding substance measurement kit of the present invention may further include a pretreatment solution for pretreating a sample as needed. In the case where the immunochromatography is employed as the sandwich method, the kit may further include a device including a zone carrying the blocked labeled lectin. The device may include other constituent elements suitable for the immunochromatography, such as a developing liquid pad and an absorption pad. Moreover, the lectin-binding substance measurement kit of the present invention may further include an instruction manual for the kit.

EXAMPLES

Hereinafter, the present invention will be described more specifically based on Examples and Comparative Examples, but the present invention should not be limited to the following Examples. In Examples and Comparative Examples, a sign "%" means weight/volume (w/v: g/mL) percent unless otherwise noted.

Example 1

Measurement of Alpha-Fetoprotein L3 Fraction (AFP-L3) Using Blocked Labeled Lectin and Labeled Lectin (1) Preparation of Hydrazinated Dextran First, 240.0 mg of dextran (manufactured by CarboMer) having a molecular weight of 250 K was added to 4.8 mL of 0.1 M phosphate buffer (pH 7.0), and was dissolved by stirring in a dark place at 25° C. for 30 minutes. Subsequently, 2.664 mL of 150 mM $NaIO_4$ and 0.536 mL of ion-exchanged water were added thereto and the mixture was stirred in a dark place at 25° C. for 30 minutes. Using a PD-10 column (manufactured by GE Healthcare, a Sephadex G-25 packed column), buffer exchange was performed with 0.1 M sodium phosphate buffer (pH 6.0) to obtain 20.0 mL of solution. Then, 5.04 g of $NH_2NH_2$—HCl was added and the mixture was stirred in a dark place at 25° C. for 2 hours. Then, 800 mg of DMAB (dimethylamine borane) was added and the mixture was further stirred in a dark place at 25° C. for 2 hours. Dialysis using an RC50K (regenerated cellulose having a molecular weight of 50,000) dialysis membrane was performed with 4 L of ion-exchanged water in a dark place for 3 hours, followed by standing at 4° C. overnight. Buffer exchange was performed by gel filtration (Sephadex G-25) using 0.1 M sodium phosphate buffer (pH 6.0) to obtain 85.0 mL of solution. The concentration of dextran was adjusted to 1.0 mg/mL, and a solution of hydrazinated dextran was obtained.

(2) Preparation of Dextran-Enzyme Conjugate 30.0 mL of 10 mg/mL alkaline phosphatase (manufactured by Oriental Yeast Co., Ltd., ALP-50) was subjected to buffer exchange by gel filtration (Sephadex G-25) using 0.1 M sodium phosphate buffer (pH 6.0) to prepare 90.6 mL of 3.0 mg/mL solution. Then, 45.3 mL of 27 mM $NaIO_4$ was added and the mixture was stirred in a dark place at 25° C. for 3 minutes. Buffer exchange was performed by gel filtration (Sephadex G-25) using 0.1 M sodium phosphate buffer (pH 6.0) to prepare 0.5 mg/mL solution. The 1.0 mg/mL hydrazinated dextran prepared in (1) of Example 1 was added such that the concentration of the hydrazide group (amino group) became 25 µM, and the mixture was stirred in a dark place at 25° C. for 16 hours. Then, 85 mg of DMAB was added and the mixture was stirred in a dark place at 25° C. for 2 hours. Subsequently, 10.1 mL of 1.5 M Tris buffer (pH 9.0) was added and the mixture was stirred in a dark place at 25° C. for 2 hours. A ultrafiltration module (Pellicon XL50, manufactured by Merck Millipore) was attached to the Labscale TFF System (manufactured by Merck Millipore) to concentrate the mixture to 15 mL, and gel filtration (Superdex 200 µg) using 0.1 M sodium phosphate buffer (pH 7.0) was carried out to obtain 14 mL of solution of 3.0 mg/mL dextran-enzyme conjugate.

(3) Maleimide-PEGylation of Dextran-Enzyme Conjugate 0.1 M sodium phosphate buffer (pH 7.0) was added to the dextran-enzyme conjugate prepared in (2) of Example 1 to prepare 750 µL of 2 mg/mL dextran-enzyme conjugate. To this, 8.35 µL of 250 mM $SM(PEG)_4$ (manufactured by Thermo Fisher Scientific, $SM(PEG)_4$) dissolved in DMSO was added and mixed, and the mixture was inverted and mixed in a dark place at 25° C. for 1 hour. After the reaction, buffer exchange using a PD-10 column (Sephadex G-25) was performed to 0.1 M sodium phosphate buffer (pH 6.3) containing 20 mM EDTA-2Na and 0.5% CHAPS. After the buffer example, the maleimide-PEGylated dextran-enzyme conjugate was concentrated using a centrifugal filter (manufactured by Merck, Amicon Ultra 50K) to adjust the final concentration to 2 mg/mL.

(4) Thiolation of Lectin

First, 5 mg of lens culinaris agglutinin (LCA; manufactured by J-CHEMICAL, Inc.) was dissolved in 2.5 mL of 0.1 M sodium phosphate buffer (pH 7.0) to obtain 2 mg/mL LCA solution. To 2.5 mL of the LAC solution, 100 µL of 0.5 M EDTA-2Na (pH 8.0) was added and mixed, and then 75 µL of 10 mg/mL 2-iminothiolane hydrochloride solution was added, followed by mixing with inversion in a dark place at 25° C. for 1 hour. After the reaction, buffer exchange using a PD-10 column (Sephadex G-25) was performed to 0.1 M sodium phosphate buffer (pH 6.3) containing 20 mM EDTA-2Na and 0.5% CHAPS. The LCA after the buffer exchange was adjusted to 650 µg/mL.

(5) Coupling

To 2 mL of the LCA thiolated and adjusted to 650 µg/mL, which was obtained in (4) of Example 1, 10 µL of 1 M glucose was added, and the mixture was inverted and mixed in a dark place at 25° C. for 30 minutes. Next, 500 µL of the solution of the maleimide-PEGylated dextran-enzyme conjugate (2 mg/mL) obtained in (3) of Example 1 was added and the mixture was inverted and mixed in a dark place at 25° C. for 1 hour, so that the LCA and the dextran-enzyme conjugate were coupled. After the reaction, 25 µL of 200 mM 3-mercapto-1,2-propanediol was added, and the mixture was inverted and mixed in a dark place at 25° C. for 30 minutes. After that, 50 µL of 200 mM 2-iodoacetamide was further added, and the mixture was inverted and mixed in a dark place at 25° C. for 30 minutes. The solution after the reaction was concentrated using a centrifugal filter (manufactured by Merck, Amicon Ultra 50K), thereafter passed through a φ0.22 µm filter, and purified by gel filtration chromatography (column: Superose 6 Increase 10/300 GL, buffer: 0.1 M MES, 0.5 M NaCl, 1 mM $MgCl_2$, 0.1 mM $ZnCl_2$, 5 mM Glucose, 0.05% CHAPS, pH 6.8), so that 2 mL of solution of 167.4 µg/mL blocked labeled lectin 1 (dextran-enzyme-LCA conjugate) was finally obtained.

(6) Preparation of Labeled Lectin

First, 5 mg of lens culinaris agglutinin (LCA; manufactured by J-CHEMICAL, Inc.) was dissolved in 1 mL of 0.1 M sodium phosphate buffer (pH 7.0) to obtain 5 mg/mL LCA solution. To 1 mL of the LAC solution, 41 µL of 10 mg/mL Sulfo-EMCS (manufactured by DOJINDO LABORATORIES) was added, and the mixture was inverted and mixed in a dark place at 25° C. for 1 hour. After the reaction, buffer exchange using a NAP-10 column (manufactured by GE Healthcare, a Sephadex G-25 packed column) was performed to 0.1 M sodium phosphate buffer (pH 6.3) containing 0.5% CHAPS, and the recovered maleimidated LCA was adjusted to a concentration of 2.5 mg/mL.

300 µL of 10 mg/mL alkaline phosphatase (manufactured by Oriental Yeast Co., Ltd., ALP-50) was subjected to buffer exchange using a NAP-5 column (manufactured by GE Healthcare, a Sephadex G-25 packed column) with 0.1 M sodium phosphate buffer (pH 7.0) to obtain 0.8 mL of 3.4 mg/mL ALP solution. Next, 13.2 µL of 10 mg/mL 2-iminothiolane hydrochloride solution was added, followed by mixing with inversion in a dark place at 25° C. for 1 hour. After the reaction, buffer exchange using a NAP-10 column (Sephadex G-25) was performed to 0.1 M sodium phosphate buffer (pH 6.0) containing 0.5% CHAPS, and the recovered thiolated ALP was adjusted to a concentration of 1.8 mg/mL.

Then, 1.07 mL of the 2.5 mg/mL maleimidated LCA and 0.83 mL of the 1.8 mg/mL thiolated ALP were mixed and allowed to stand in a dark place at 25° C. for 20 hours to couple the LCA and the ALP. After the reaction, 19 ML of 150 mM 3-mercapto-1,2-propanediol was added and the mixture was allowed to stand in a dark place at 25° C. for 1 hour. The solution after the reaction was concentrated using a centrifugal filter (manufactured by Merck, Amicon Ultra 50K), thereafter passed through a φ0.22 µm filter, and purified by gel filtration chromatography (column: Superdex 200 PG, buffer: 0.1 M MES, 0.15 M NaCl, 1 mM $MgCl_2$, 1 mM $ZnCl_2$, 0.3 M Methyl-α-D-mannopyranoside, 0.05% CHAPS, 0.9% $NaN_3$, pH 6.8), so that 1 mL of solution of 543 µg/mL labeled lectin 1 (ALP-LCA conjugate) was finally obtained.

(7) Measurement of AFP-L3

Magnetic particles (manufactured by FUJIREBIO Inc.) and anti-AFP monoclonal antibody $F(ab')_2$ fragments (manufactured by FUJIREBIO Inc.) were reacted to immobilize the antibody fragments on the particles. The particles on which the antibody fragments were immobilized were diluted at a particle concentration of 0.01% with a particle diluent (50 mM Tris, 100 mM KCl, 0.5% BSA, pH 7.2) to prepare a solution of anti-AFP antibody F(ab')$_2$ fragment-binding particles.

As a sample, a cancer-mutated AFP antigen (Huh7 cell culture serum-free supernatant, an AFP-L3 content rate of 93.3%, hereinafter also referred to as "L3 antigen") was diluted with Carbo-Free Blocking Solution (CFB; manufactured by VECTOR) at 1.6, 3.1, 6.3, 12.5, 25, 50, 100, or 200 ng/mL to prepare each L3 antigen analyte solution. In addition, a healthy person AFP antigen (manufactured by Lee Biosolutions, an AFP-L3 content rate of 7.8%, hereinafter also referred to as "L1 antigen") was diluted at 200 ng/mL with CFB to prepare an L1 antigen analyte solution as a reference sample.

Each of the blocked labeled lectin 1 obtained in (5) of Example 1 and the labeled lectin 1 obtained in (6) of Example 1 was diluted at 0.5 µg/mL with a label diluent (30 mM MES, 360 mM NaCl, 1.5% arginine, 0.06% hydrazine hydrochloride, 0.06 mM ZnCl$_2$, 0.6 mM MgCl$_2$, 30 µg/mL inactivated ALP, 30 µg/mL Mouse KLG, 2.4% C14APS, 0.15% Tween 20, 1×CFB, 1% Tergitol 15-s-7, 0.0005% Antiform SI), thereby preparing label solutions of the blocked labeled lectin 1 solution and the labeled lectin 1 solution. To each of the label solutions, free dextran 2000K (manufactured by Sigma) was added at 0%, 1.0%, 2.0%, or 3.0%.

AFP-L3 was measured using Lumipulse (registered trademark) L-2400 (manufactured by FUJIREBIO Inc.) for the above-mentioned L1 antigen analyte solution and L3 antigen analyte solution. Here, 50 µL of each of the analyte solutions and 50 µL of the aforementioned solution of anti-AFP antibody F(ab')$_2$ fragment-binding particles were mixed and reacted at 37° C. for 8 minutes. Next, the magnetic particles were collected and washed five times with a Lumipulse (registered trademark) washing liquid (manufactured by FUJIREBIO Inc.). Subsequently, 50 µL of each of the aforementioned label solutions was added, followed by reaction at 37° C. for 8 minutes. Next, after the magnetic particles were collected and washed five times, 50 µL of a Lumipulse (registered trademark) substrate solution containing AMPPD (3-(2'-spiroadamantane)-4-methoxy-4-(3'-phosphoryloxy)phenyl-1,2-dioxetane-2-sodium salt) (manufactured by FUJIREBIO Inc.) was added, followed by reaction at 37° C. for 4 minutes. The amount of light with maximum absorption at a wavelength of 463 nm emitted by the decomposition of AMPPD by the catalytic action of the alkaline phosphatase of the blocked labeled lectin 1 or the labeled lectin 1 bound to the magnetic particles was measured. The measurement results were each output by an emission intensity (count) of the substrate. The measurement results under the respective conditions are shown in Table 1 presented below. Note that each of the presented results indicates a value obtained by subtracting a blank value obtained by measuring only the buffer from the average value in dual measurement.

TABLE 1

|  |  | Ex. 1-1 | Ex. 1-2 | Ex. 1-3 | Ex. 1-4 | Comp. Ex. 1-1 | Comp. Ex. 1-2 | Comp. Ex. 1-3 | Comp. Ex. 1-4 |
|---|---|---|---|---|---|---|---|---|---|
| Label |  | Blocked Labeled Lectin 1 | | | | Labeled Lectin 1 | | | |
| Free Dextran Concentration [%] |  | 0 | 1.0 | 2.0 | 3.0 | 0 | 1.0 | 2.0 | 3.0 |
| Antigen | Concentration [ng/mL] |  |  |  |  |  |  |  |  |
| L3 Antigen | 200 | 335837 | 778428 | 1269328 | 1539225 | 20191 | 25949 | 37149 | 50376 |
|  | 100 | 130144 | 438927 | 866745 | 1115575 | 3977 | 5534 | 8372 | 10102 |
|  | 50 | 44119 | 144108 | 425227 | 675359 | 1006 | 1690 | 2949 | 3148 |
|  | 25 | 10924 | 46589 | 174226 | 367657 | 559 | 816 | 1601 | 993 |
|  | 12.5 | 6185 | 13324 | 43716 | 164340 | 102 | 139 | 1024 | 447 |
|  | 6.3 | 4976 | 7461 | 17861 | 79625 | 248 | 110 | 989 | 0 |
|  | 3.1 | 2995 | 639 | 10565 | 39566 | 356 | 160 | 1061 | 0 |
|  | 1.6 | 108 | 466 | 824 | 10003 | 244 | 0 | 1141 | 0 |
| L1 Antigen | 200 | 0 | 0 | 0 | 0 | 0 | 0 | 0 | 0 |

As shown in Table 1, it is confirmed that both of the blocked labeled lectin 1 and the labeled lectin 1 hardly bind to the L1 antigen but bind to the L3 antigen. In particular, in the case of using the blocked labeled lectin 1 of the present invention (Examples 1-1 to 1-4), the signals obtained are higher than in the case of using the labeled lectin 1 (Comparative Examples 1-1 to 1-4), which suggests that measurement with higher sensitivity is possible. Moreover, it is confirmed that, in the case where the free dextran is added to each of the label solutions, the signals obtained by using the blocked labeled lectin 1 achieve the significantly high values as compared with the labeled lectin 1.

Example 2

Measurement of Prostate Cancer Cell-Derived PSA Using Blocked Labeled Lectin and Labeled Lectin 1

(1) Preparation of Blocked Labeled Lectin Using AAL 20 ml of solution of 87.8 µg/mL blocked labeled lectin 2 (dextran-enzyme-AAL conjugate) was obtained in the same manner as in (1) to (5) of Example 1 except that aleuria aurantia lectin (AAL; manufactured by VECTOR) was used instead of the lens culinaris agglutinin (LCA).

(2) Preparation of Labeled Lectin Using AAL 20 ml of solution of 34.4 µg/mL labeled lectin 2 (ALP-AAL conjugate) was obtained in the same manner as in (6) of Example 1 except that the aleuria aurantia lectin (AAL; manufactured by VECTOR) was used instead of the lens culinaris agglutinin (LCA).

(3) Measurement of Cancer Cell-Derived PSA

Magnetic particles (manufactured by FUJIREBIO Inc.) and anti-PSA monoclonal antibody F(ab')$_2$ fragments (manufactured by FUJIREBIO Inc.) were reacted to immobilize the antibody fragments on the particles. The particles on which the antibody fragments were immobilized were diluted at a particle concentration of 0.01% with a particle diluent (50 mM Tris, 100 mM KCl, 0.5% BSA, pH 7.2) to prepare a solution of anti-PSA antibody F(ab')$_2$ fragment-binding particles.

Any of the blocked labeled lectin 2 (dextran-enzyme-AAL conjugate) obtained in (1) of Example 2 and the labeled lectin 2 (ALP-AAL conjugate) obtained in (2) of Example 2 was added at 0.5 μg/mL to PBS (pH 7.4) containing 1.0% BSA, 2.0% free dextran 2000K, and 0.0005% Antiform SI, thereby preparing each of the label solutions of the blocked labeled lectin 2 and the labeled lectin 2. As a sample, cultured prostate cancer cell (LNCaP)-derived PSA (LNCap-PSA) was diluted with CFB to prepare an analyte solution having a concentration of LNCap-PSA of 50 ng/mL.

The cancer cell-derived PSA was measured in the same manner as in (7) of Example 1 except that the label solutions, the analyte solution, and the solution of anti-PSA antibody F(ab')$_2$ fragment-binding particles described above were used. The measurement results of the cancer cell-derived PSA under the respective conditions (an emission intensity (count) of the substrate) are shown in Table 2 presented below. Note that each of the presented results indicates a value obtained by subtracting a blank value obtained by measuring only the buffer from the average value in dual measurement.

TABLE 2

|  | Ex. 2-1 | Comp. Ex. 2-1 |
| --- | --- | --- |
| Label | Blocked Labeled Lectin 2 | Labeled Lectin 2 |
| LNCap-PSA [50 ng/mL] | 15319176 | 628466 |

Table 2 indicates that both of the blocked labeled lectin 2 and the labeled lectin 2 are capable of detecting the cancer cell-derived PSA. In particular, in the case of using the blocked labeled lectin 2 (Example 2-1), the signal obtained is higher than in the case of using the labeled lectin 2 (Comparative Example 2-1), which suggests that measurement with higher sensitivity is possible.

Example 3

Measurement of AFP-L3 Using Mixture of Plural Blocked Labeled Lectins (1) Preparation of Blocked Labeled Lectins Each blocked labeled lectin was prepared in the same manner as in (1) to (5) of Example 1 except that dextran having a molecular weight of 500K (manufactured by Fluka) or dextran having a molecular weight of 70K (manufactured by TCI) was used as the dextran. The blocked labeled lectin obtained by using the dextran having a molecular weight of 500K is referred to as "blocked labeled lectin 3 (500K)" and the blocked labeled lectin obtained by using the dextran having a molecular weight of 70K is referred to as "blocked labeled lectin 4 (70K)".

(2) Measurement of AFP-L3 1

A solution of anti-AFP antibody F(ab')$_2$ fragment-binding particles was prepared in the same manner as in (7) of Example 1 except that the composition of the particle diluent was 50 mM Tris, 150 mM NaCl, 2 mM EDTA-2Na, 0.5 mg/mL Sodium Dextran Sulfate 5,000, 30 μg/mL Mouse KLG, 1.0% BSA, 0.005% Antiform SI, 0.1% ProClin 300, and pH 7.2.

In addition, each analyte solution was prepared in the same manner as in (7) of Example 1 except that the L3 antigen was diluted at a concentration of 1.0, 2.0, 3.9, 7.8, 15.6, 31.3, 62.5, 125, or 250 ng/mL.

The blocked labeled lectin 3 (500K), the blocked labeled lectin 4 (70K), and the labeled lectin 1 obtained in (6) of Example 1 were each diluted at 0.5 μg/mL with a label diluent (30 mM MES, 360 mM NaCl, 1.5% arginine, 0.06% hydrazine hydrochloride, 0.06 mM ZnCl$_2$, 0.6 mM MgCl$_2$, 30 μg/mL Inactivated ALP, 30 μg/mL Mouse KLG, 2.4% C14APS, 0.15% Tween 20, 1×CFB, 1% Tergitol 15-s-7, 1.0% free dextran 2000K, 50 μg/mL free LCA, and 0.0005% Antiform SI), to prepare three kinds of label solutions of the blocked labeled lectin 3 (500K) solution, the blocked labeled lectin 4 (70K) solution, and the labeled lectin 1 solution.

AFP-L3 was measured in the same manner as in (7) of Example 1 except that the label solutions, the analyte solutions, and the solution of anti-AFP antibody F(ab')$_2$ fragment-binding particles described above were used. The measurement results of AFP-L3 under the respective conditions (an emission intensity (count) of the substrate) are shown in Table 3 presented below. Note that each of the presented results indicates a value obtained by subtracting a blank value obtained by measuring only the buffer from the average value in dual measurement.

TABLE 3

|  |  | Ex. 3-1 | Ex. 3-2 | Comp. Ex. 3-1 |
| --- | --- | --- | --- | --- |
| Label |  | Blocked Labeled Lectin 3 (500K) | Blocked Labeled Lectin 4 (70K) | Labeled Lectin 1 |
| Antigen | Concentration [ng/mL] |  |  |  |
| L3 Antigen | 250 | 1864440 | 1444227 | 93067 |
|  | 125 | 990488 | 800996 | 18330 |
|  | 62.5 | 516207 | 348412 | 4045 |
|  | 31.3 | 189700 | 104907 | 1535 |
|  | 15.6 | 69782 | 36211 | 684 |
|  | 7.8 | 31079 | 11233 | 780 |
|  | 3.9 | 15024 | 4664 | 305 |
|  | 2.0 | 6044 | 2077 | 471 |
|  | 1.0 | 2805 | 116 | 125 |

As shown in Table 3, both of the blocked labeled lectin 3 (500K) (Example 3-1) and the blocked labeled lectin 4 (70K) (Example 3-2) detected the L3 antigen with much higher sensitivity than the labeled lectin 1 (Comparative Example 3-1), and in particular, the blocked labeled lectin 3 (500K) detected the L3 antigen with even higher sensitivity than the blocked labeled lectin 4 (70K). These results demonstrate that use of the blocked labeled lectin of the present invention makes it possible to measure a measurement target substance (AFP-L3) with higher sensitivity than the labeled lectin and further demonstrate that use of dextran having a larger molecular size in preparation of the blocked labeled lectin makes it possible to measure a measurement target substance with much higher sensitivity, even when the concentration of the measurement target substance is low.

(3) Measurement of AFP-L3 2

Analyte solutions were prepared in the same manner as in (7) of Example 1 except that the L3 antigen was diluted at each of concentrations (2.0 to 2000 ng/mL) specified in Table 4 presented below. The blocked labeled lectin 3 (500K), the blocked labeled lectin 4 (70K), and the labeled lectin 1 obtained in (6) of Example 1 at concentrations and in each of combinations specified in Table 4 presented below were diluted at 0.5 μg/mL with a label diluent (30 mM MES, 360 mM NaCl, 1.5% arginine, 0.06 mM $ZnCl_2$, 0.6 mM $MgCl_2$, 2.4% C14APS, 0.15% Tween 20, 1×CFB, 1% Tergitol 15-s-7, 1% free dextran 2000K, 50 μg/mL free LCA, 0.0005% Antiform SI) to prepare three kinds of label solutions of the blocked labeled lectin 3 (500K) solution, the blocked labeled lectin 4 (70K) solution, and the labeled lectin 1 solution.

AFP-L3 was measured in the same manner as in (7) of Example 1 except that the analyte solutions and the label solutions described above were used. The measurement results of AFP-L3 under the respective conditions (an emission intensity (count) of the substrate) are shown in Table 4 presented below and FIG. 1. Note that each of the presented results indicates a value obtained by subtracting a blank value obtained by measuring only the buffer from the average value in dual measurement.

liquid. Then, 200 μL of an eluate (0.1 M Glycine, 0.3 M NaCl, 0.2% Triton X-100, 1×CFB, pH 2.1) was added, and the mixture was stirred and shaken at room temperature for 20 seconds. The supernatant was transferred to another container and neutralized by adding 10 μL of 2 M Tris (pH 10.0), and then 90 μL of CFB was added to prepare a purified sample.

(2) Measurement of AFP-L3

Each of the blocked labeled lectin 1 obtained in (5) of Example 1 and the labeled lectin 1 obtained in (6) of Example 1 was diluted at 0.5 μg/mL with a label diluent (30 mM MES, 360 mM NaCl, 1.5% arginine, 0.06 mM $ZnCl_2$, 0.6 mM $MgCl_2$, 30 μg/mL Inactivated ALP, 30 μg/mL Mouse KLG, 2.4% C14APS, 0.15% Tween 20, 1×CFB, 1% Tergitol 15-s-7, 2% free dextran 2000K, 0.0005% Antiform SI), thereby preparing each of label solutions of the blocked labeled lectin 1 solution and the labeled lectin 1 solution.

TABLE 4

|  |  | Ex. 3-3 | Ex. 3-4 | Ex. 3-5 | Ex. 3-6 |
|---|---|---|---|---|---|
| Label [ng/mL] | Blocked Labeled Lectin 3 (500K) | 0.5 | 0.5 | 0.5 | 0.5 |
|  | Blocked Labeled Lectin 4 (70K) | 0 | 0.25 | 0 | 0.25 |
|  | Labeled Lectin 1 | 0 | 0 | 0.25 | 0.25 |
| Antigen | Concentration [ng/mL] |  |  |  |  |
| L3 Antigen | 2000 | 2494264 | 3136098 | 3505041 | 3893738 |
|  | 1500 | 2344081 | 3070839 | 3400634 | 3811630 |
|  | 1000 | 2270692 | 2821063 | 3116026 | 3601364 |
|  | 500 | 1902917 | 2179683 | 2730099 | 2701761 |
|  | 250 | 1478825 | 1435540 | 1815890 | 1725811 |
|  | 125 | 797557 | 896513 | 991908 | 952317 |
|  | 62.5 | 368050 | 388683 | 413120 | 389270 |
|  | 31.3 | 146586 | 152857 | 130413 | 121342 |
|  | 15.6 | 43243 | 55902 | 52549 | 51556 |
|  | 7.8 | 15174 | 14437 | 20409 | 13932 |
|  | 3.9 | 11990 | 8242 | 9479 | 11125 |
|  | 2.0 | 2666 | 14228 | 5112 | 0 |

As shown in Table 4 and FIG. 1, it is observed that when the combination of the plural blocked labeled lectins containing dextrans different in molecular weight, or the combination further including the labeled lectin is capable of achieving more accurate quantification of an analyte containing a measurement target substance (AFP-L3) even at a high concentration, in particular.

Example 4

Purification Treatment of Sample in AFP-L3 Measurement in Serum

As samples, CFB containing 200 ng/mL L3 antigen (B1, buffer analyte), healthy person serum to which L3 antigen was added at 200 ng/mL (S1, serum analyte), and healthy person serum to which no L3 antigen was added (S2, serum analyte) were prepared.

(1) Sample Purification Treatment

40 μL of anti-AFP antibody-binding particles (manufactured by FUJIREBIO Inc.) and 300 μL of each of the serum analytes (S1 or S2) were mixed, and the mixture was stirred and shaken at room temperature for 40 seconds. After the magnetic particles were collected and the supernatant was removed, the magnetic particles were washed three times with 300 μL of a Lumipulse (registered trademark) washing AFP-L3 in S1 and S2 purified by the purification treatment in (1) of Example 4 was measured in the same manner as in (7) of Example 1 except that the label solutions described above were used. In addition, AFP-L3 in S1, S2, and B1 was measured under the condition where the purification treatment in (1) of Example 4 was not performed and the other conditions set to the same as the above. The measurement results of AFP-L3 under the respective conditions (an emission intensity (count) of the substrate) are shown in Table 5 presented below. Note that each of the presented results indicates a value obtained by subtracting a blank value obtained by measuring only the buffer from the average value in dual measurement.

TABLE 5

|  | Ex. 4-1 | Comp. Ex. 4-1 |
|---|---|---|
| Label | Blocked Labeled Lectin 1 | Labeled Lectin 1 |

TABLE 5-continued

|  |  | Ex. 4-1 | Comp. Ex. 4-1 |
|---|---|---|---|
| Purification Treatment Not Purified | Sample B1 | 558150 | 63707 |
|  | S1 | 797593 | 438732 |
|  | S2 | 489568 | 382116 |
| Purified | S1 | 526653 | 131836 |
|  | S2 | 21680 | 12556 |

As shown in Table 5, a high signal was detected in the healthy person serum analyte (S2) under the condition where the purification treatment was not performed. However, in the case of using the blocked labeled lectin 1 of the present invention (Example 4-1), the signal obtained from the serum analyte (S1) containing a larger amount of AFP-L3 is higher than in the case of using the labeled lectin 1 (Comparative Example 4-1). Therefore, it is confirmed that the blocked labeled lectin is sufficiently capable of detection itself of the measurement target substance (AFP-L3). As a result of the purification treatment, the signal from the serum analyte (S1) containing the larger amount of AFP-L3 was also decreased but the signal from the healthy person serum analyte (S2) was remarkably decreased, which suggests that it is possible to measure the measurement target substance with higher accuracy.

Example 5

Evaluation of Lectin Species of Blocked Labeled Lectin and Evaluation of Specificity for Prostate Cancer Cell-Derived PSA 1

(1) Preparation of Blocked Labeled Lectin Using MAM 3.5 mL of 182.7 μg/mL blocked labeled lectin 5 (MAM) (dextran-enzyme-MAM conjugate) was obtained in the same manner as in (1) to (5) of Example 1 except that *Maackia amurensis* leukoagglutinin lectin (*Maackia amurensis* lectin I, MAM; manufactured by J-CHEMICAL, Inc.) was used instead of the lens culinaris agglutinin (LCA).

(2) Measurement of Cancer Cell-Derived PSA

In each well of a 96-well microwell plate (Nunc MAXISORP, black, 16-well module×4), 50 μL/well of PBS (pH 7.4) containing 0.1 μg/mL cultured prostate cancer cell (LNCaP)-derived PSA (LNCap-PSA) or 0.1 μg/mL human seminal fluid (HSF)-derived PSA (HSF-PSA), or PBS (pH 7.4) containing none of the PSAs and only containing 1.0% BSA was dispensed as a sample. After incubation at 37° C. for 1.5 hours, the samples were washed three times with PBST (0.1% Tween 20 in PBS, pH 7.4) and one time with PBS (pH 7.4). Then, 150 μL/well of a blocking solution (1.0% BSA/PBS, pH 7.4) was dispensed, and the samples were allowed to stand at 37° C. for 2 hours and then stored at 4° C.

After the blocking solution was removed, 50 μL/well of PBS (pH 7.4) containing 0.5 μg/mL blocked labeled lectin 5 (MAM), 1.0% BSA, and 0% to 3.0% free dextran 2000K was dispensed, followed by incubation at 37° C. for 1.5 hours and thereafter washing three times with PBST and then one time with PBS (pH 7.4). Next, 50 μL/well of a Lumipulse (registered trademark) substrate solution preheated to 37° C. was dispensed, and 5 minutes later, the amount of light emitted with maximum absorption at a wavelength of 463 nm was measured with a microplate reader. The measurement results were each output by an emission intensity (count) of the substrate. The measurement results under the respective conditions are shown in Table 6 presented below. Note that each of the presented results indicates the average value in dual measurement.

TABLE 6

| Immobilized Antigen | Free Dextran Concentration [%] | Count |
|---|---|---|
| LNCap-PSA | 0 | 543695 |
|  | 0.5 | 670400 |
|  | 1.0 | 821588 |
|  | 2.0 | 1021808 |
|  | 3.0 | 1027570 |
| HSF-PSA | 0 | 5813 |
|  | 0.5 | 7940 |
|  | 1.0 | 8253 |
|  | 2.0 | 13305 |
|  | 3.0 | 30950 |
| BSA | 0 | 5415 |
|  | 0.5 | 7168 |
|  | 1.0 | 12078 |
|  | 2.0 | 19303 |
|  | 3.0 | 47355 |

As shown in Table 6, strong signals were detected only on the plate on which LNCap-PSA was immobilized. In addition, it is observed the signals were further enhanced under the condition containing the free dextran. On the other hand, the signals on the plate on which HSF-PSA was immobilized and the plate on which BSA was immobilized have almost no difference, which suggests that the blocked labeled lectin 5 (MAM) hardly reacts with HSF-PSA. These results confirm that the blocked labeled lectin of the present invention specifically binds to cancer-derived PSA even when using the *Maackia amurensis* lectin I (MAM) as a lectin.

Example 6

Evaluation of Lectin Species of Blocked Labeled Lectin and Evaluation of Specificity for Prostate Cancer Cell-Derived PSA 2

(1) Preparation of Blocked Labeled Lectin Using WFA 2.0 mL of 373.9 μg/mL blocked labeled lectin 6 (WFA) (dextran-enzyme-WFA conjugate) was obtained in the same manner as in (1) to (5) of Example 1 except that wisteria floribunda agglutinin (WFA; manufactured by VECTOR) was used instead of the lens culinaris agglutinin (LCA).

(2) Measurement of Cancer Cell-Derived PSA

Magnetic particles (manufactured by FUJIREBIO Inc.) and anti-PSA monoclonal antibody F(ab')$_2$ fragments (manufactured by FUJIREBIO Inc.) were reacted to immobilize the antibody fragments on the particles. The particles on which the antibody fragments were immobilized were diluted at a particle concentration of 0.01% with a particle diluent (50 mM Tris, 100 mM KCl, 0.5% BSA, pH 7.2) to prepare a solution of anti-PSA antibody F(ab')$_2$ fragment-binding particles.

To PBS (pH 7.4) containing 1.0% BSA and 0.5 μg/mL of any of the blocked labeled lectin 5 (MAM) (dextran-enzyme-MAM conjugate) obtained in (1) of Example 5, the blocked labeled lectin 2 (AAL) (dextran-enzyme-AAL conjugate) obtained in (1) of Example 2, and the blocked labeled lectin 6 (WFA) (dextran-enzyme-WFA conjugate) obtained in (1) of Example 6, 0%, 1.0%, or 2.0% free dextran 2000K was added, thereby preparing each of the label solutions of the blocked labeled lectins 2, 5, and 6. In addition, LNCap-PSA (cultured prostate cancer cell-derived PSA) was diluted at 1.6, 3.1, 6.3, 12.5, 25, or 50 ng/mL with CFB to prepare each analyte solution as a sample.

The cancer cell-derived PSA was measured in the same manner as in (7) of Example 1 except that the label solutions, the analyte solutions, and the solution of anti-PSA antibody F(ab')$_2$ fragment-binding particles described above were used. The measurement results of the cancer cell-derived PSA under the respective conditions (an emission intensity (count) of the substrate) are shown in Table 7 presented below. Note that each of the presented results indicates a value obtained by subtracting a blank value obtained by measuring only the buffer from the average value in dual measurement.

TABLE 7

| | | Ex. 6-1 | Ex. 6-2 | Ex. 6-3 | Ex. 6-4 | Ex. 6-5 | Ex. 6-6 | Ex. 6-7 | Ex. 6-8 | Ex. 6-9 |
|---|---|---|---|---|---|---|---|---|---|---|
| Label 1 | | Blocked Labeled Lectin 5 (MAM) | | | Blocked Labeled Lectin 2 (AAL) | | | Blocked Labeled Lectin 6 (WFA) | | |
| Free Dextran Concentration [%] | | 0 | 1.0 | 2.0 | 0 | 1.0 | 2.0 | 0 | 1.0 | 2.0 |
| Antigen | Concentration [ng/mL] | | | | | | | | | |
| LNCap-PSA | 50 | 11329 | 32748 | 83585 | 1507401 | 4521804 | 11907068 | 370637 | 1046139 | 3061645 |
| | 25 | 5319 | 17221 | 42500 | 405187 | 1196699 | 3922358 | 77907 | 250601 | 869272 |
| | 12.5 | 2427 | 8438 | 22203 | 145151 | 409077 | 1331287 | 19614 | 57181 | 204477 |
| | 6.3 | 1424 | 4890 | 10222 | 120125 | 307276 | 876801 | 9019 | 21081 | 59982 |
| | 3.1 | 822 | 2829 | 5962 | 28658 | 82907 | 229765 | 5047 | 10571 | 29252 |
| | 1.6 | 374 | 1233 | 2458 | 15930 | 40423 | 109563 | 2585 | 5379 | 15427 |

As shown in Table 7, it is confirmed that the blocked labeled lectin of the present invention is capable of specifically binding to the cancer cell-derived PSA even when using any of the *Maackia amurensis* lectin I (MAM), the aleuria aurantia lectin (AAL), and the wisteria floribunda agglutinin (WFA) as a lectin. In addition, it is also confirmed that the addition of the free dextran to the label solutions especially remarkably enhances the signals detecting the cancer cell-derived PSA.

Example 7

Measurement of Prostate Cancer Cell-Derived PSA Using Blocked Labeled Lectin and Labeled Lectin 2

(1) Preparation of Blocked Labeled Lectin Using MAM

A solution of blocked labeled lectin 7 (dextran 500K-enzyme-MAM conjugate: "blocked labeled lectin 7 (500K)") was obtained in the same manner as in (1) to (5) of Example 1 except that the *Maackia amurensis* leukoagglutinin lectin (*Maackia amurensis* lectin I: MAM; manufactured by J-CHEMICAL, INC.) was used instead of the lens culinaris agglutinin (LCA) and the dextran having a molecular weight of 500K (manufactured by Fluka) was used as the dextran.

(2) Preparation of Labeled Lectin Using MAM

A solution of labeled lectin 3 (ALP-MAM conjugate) was obtained in the same manner as in (6) of Example 1 except that the *Maackia amurensis* leukoagglutinin lectin (*Maackia amurensis* lectin I: MAM; manufactured by J-CHEMICAL, INC.) was used instead of the lens culinaris agglutinin (LCA).

(3) Measurement of Cancer Cell-Derived PSA

Any of the blocked labeled lectin 5 (MAM) (dextran 250K-enzyme-MAM conjugate: "blocked labeled lectin 5 (250K)") obtained in (1) of Example 5, the blocked labeled lectin 7 (500K) obtained in (1) of Example 7, and the labeled lectin 3 obtained in (2) of Example 7 was added at 0.5 µg/mL to a diluent solution (PBS containing 1.0% BSA, 2.0% free dextran 2000K, and 0.0005% Antiform SI, pH 7.4), thereby preparing each of the label solutions of the blocked labeled lectin 5 (250K), the blocked labeled lectin 7 (500K), and the labeled lectin 3. In addition, LNCap-PSA (cultured prostate cancer cell-derived PSA) was diluted at 1.56, 3.13, 6.25, 12.5, 25, or 50 ng/mL with CFB to prepare each analyte solution as a sample.

The cancer cell-derived PSA was measured in the same manner as in (2) of Example 6 except that the label solutions and the analyte solutions described above were used. The measurement results under the respective conditions (an emission intensity (count) of the substrate) are shown in Table 8 presented below. Each of the presented results indicates a value obtained by subtracting a blank value obtained by measuring only the buffer from the average value in dual measurement.

TABLE 8

| | | Ex. 7-1 | Ex. 7-2 | Comp. Ex. 7-1 |
|---|---|---|---|---|
| Label | | Blocked Labeled Lectin 5 (250K) | Blocked Labeled Lectin 7 (500K) | Labeled Lectin 3 |
| Antigen | Concentration [ng/mL] | | | |
| LNCap-PSA | 50 | 420949 | 1351856 | 1877 |
| | 25 | 202236 | 727777 | 914 |
| | 12.5 | 97236 | 385762 | 628 |
| | 6.25 | 49826 | 180710 | 257 |
| | 3.13 | 18389 | 88413 | 104 |
| | 1.56 | 5993 | 45010 | 15 |

As shown in Table 8, both of the blocked labeled lectin 5 (250K) (Example 7-1) and the blocked labeled lectin 7 (500K) (Example 7-2) detected LNCap-PSA with much higher sensitivity than the labeled lectin 3 (Comparative Example 7-1), and in particular, the blocked labeled lectin 7 (500K) detected LNCap-PSA with even higher sensitivity than the blocked labeled lectin 5 (250K). These results demonstrate that use of the blocked labeled lectin of the present invention makes it possible to measure a measurement target substance (LNCap-PSA) with higher sensitivity than the labeled lectin and further demonstrate that use of dextran having a larger molecular size in preparation of the blocked labeled lectin makes it possible to measure a measurement target substance with much higher sensitivity, even when the concentration of the measurement target substance is low.

Example 8

Measurement of Prostate Cancer Cell-Derived PSA Using Blocked Labeled Lectin (WFA)

(1) Measurement of Cancer Cell-Derived PSA

Each of LNCap-PSA (cultured prostate cancer cell-derived PSA) and HSF-PSA (human seminal fluid-derived PSA) was diluted at 0.39, 0.78, 1.56, 3.13, 6.25, 12.5, 25, or 50 ng/mL with CFB to prepare each analyte solution as a sample.

The cancer cell-derived PSA was measured in the same manner as in (2) of Example 6 in which the blocked labeled lectin 6 (WFA) was used, except that these analyte solutions were used. The measurement results under the respective conditions (an emission intensity (count) of the substrate) are shown in Table 9 presented below. Note that each of the presented results indicates a value obtained by subtracting a blank value obtained by measuring only the buffer from the average value in dual measurement.

TABLE 9

| Concentration [ng/mL] | Label Blocked Labeled Lectin 6 (WFA) Antigen | |
|---|---|---|
| | HSF-PSA | LNCap-PSA |
| 50 | 9444 | 6162495 |
| 25 | 5734 | 1932243 |
| 12.5 | 1998 | 503913 |
| 6.25 | 673 | 159445 |
| 3.13 | 530 | 54944 |
| 1.56 | 409 | 20562 |
| 0.78 | 0 | 9961 |
| 0.39 | 444 | 5626 |

As shown in Table 9, strong signals were detected when LNCap-PSA was measured. As compared with them, signals obtained when HSF-PSA was measured are very weak, which suggests that the blocked labeled lectin 6 (WFA) hardly reacts with HSF-PSA. These results confirm that the blocked labeled lectin of the present invention specifically binds to cancer-derived PSA even when using wisteria floribunda agglutinin (WFA) as a lectin.

Example 9

Measurement of Prostate Cancer Cell-Derived PSA Using Mixture of Blocked Labeled Lectin (WFA) and Labeled Lectin (1) Preparation of Labeled Lectin Using WFA A solution of labeled lectin 4 (ALP-WFA conjugate) was obtained in the same manner as in (6) of Example 1 except that the wisteria floribunda agglutinin (WFA; manufactured by VECTOR) was used instead of the lens culinaris agglutinin (LCA).

(2) Measurement of Cancer Cell-Derived PSA

Any of the blocked labeled lectin 6 (WFA) obtained in (1) of Example 6 and the labeled lectin 4 obtained in (1) of Example 9 was added at 0.5 µg/mL to a diluent solution, thereby preparing each of the label solutions of the blocked labeled lectin 6 and the labeled lectin 4. In addition, the blocked labeled lectin 6 (WFA) and the labeled lectin 4 were added at 0.5 µg/mL and 0.25 µg/mL, respectively, to a diluent solution, thereby preparing the label solution of the mixture of the blocked labeled lectin 6 and the labeled lectin 4. Then, LNCap-PSA (cultured prostate cancer cell-derived PSA) was diluted at 1, 5, 10, 25, or 50 ng/mL with healthy person serum to prepare each analyte solution as a sample.

The cancer cell-derived PSA was measured in the same manner as in (2) of Example 6 except that the label solutions and the analyte solutions described above were used. The measurement results of the cancer cell-derived PSA under the respective conditions (an emission intensity (count) of the substrate) are shown in Table 10 presented below. Note that each of the presented results indicates a value obtained by subtracting a blank value obtained by measuring only healthy person serum from the average value in dual measurement.

TABLE 10

| | | Comp. Ex. 9-1 | Ex. 9-1 | Ex. 9-2 |
|---|---|---|---|---|
| Label [ng/mL] | Blocked Labeled Lectin 6 (WFA) | 0 | 0.5 | 0.5 |
| | Labeled Lectin 4 | 0.5 | 0 | 0.25 |
| Antigen Concentration [ng/mL] | | | | |
| LNCap-PSA | 50 | 978876 | 2864288 | 4863439 |
| | 25 | 181343 | 522615 | 972000 |
| | 10 | 26756 | 44242 | 86002 |
| | 5 | 23701 | 32078 | 74046 |
| | 1 | 9480 | 10662 | 33653 |

As shown in Table 10, the blocked labeled lectin 6 (WFA) (Example 9-1) detected LNCap-PSA with much higher sensitivity than the labeled lectin 4 (Comparative Example 9-1). In addition, it is confirmed that the combination of the blocked labeled lectin 6 (WFA) and the labeled lectin 4 (Example 9-2) achieves more accurate quantification even in the analyte containing the measurement target substance (LNCap-PSA) at a high concentration, in particular.

INDUSTRIAL APPLICABILITY

According to the present invention, it is possible to provide a lectin-binding substance measurement method and a lectin-binding substance measurement kit which are capable of measuring a lectin-binding substance in a sample with high sensitivity in a simple procedure, and provide a blocked labeled lectin for use in these.

The invention claimed is:

1. A lectin-binding substance measurement method for measuring a lectin-binding substance in a sample, the method comprising
a measuring step of bringing a blocked labeled lectin and a labeled lectin into contact with the sample, wherein the blocked labeled lectin is a combination of
a high molecular weight blocked labeled lectin including a first water-soluble carrier made of a high molecular weight water-soluble polymer having a weight average molecular weight of 200,000 or more, and a first labeling substance and a first lectin immobilized on the first water-soluble carrier and
a low molecular weight blocked labeled lectin including a second water-soluble carrier made of a low molecular weight water-soluble polymer having a weight average molecular weight of less than 100, 000, and a second labeling substance and a second lectin immobilized on the second water-soluble carrier, the labeled lectin comprises a third labeling substance and a third lectin, and excludes any water-soluble carrier, the high molecular weight water-soluble polymer and the low molecular weight water soluble polymer are comprised of a same or different class of polymer, the first labeling substance, the second labeling substance, and the third labeling substance are a same or different labeling substance, and the first lectin, the second lectin, and the third lectin are a same or different lectin.

2. The lectin-binding substance measurement method according to claim 1, wherein the measuring step is carried out in the presence of a free water-soluble polymer.

3. The lectin-binding substance measurement method according to claim 2, wherein the high molecular weight water-soluble polymer and the low molecular weight water-soluble polymer are comprised of a same class of polymer.

4. The lectin-binding substance measurement method according to claim 3, wherein the free water-soluble polymer is the same class of polymer as the high molecular weight water soluble polymer and the low molecular weight water-soluble polymer.

5. The lectin-binding substance measurement method according to claim 1, wherein
the high molecular weight water-soluble polymer of the high molecular weight blocked labeled lectin is dextran having the weight average molecular weight of 200,000 or more, and the low molecular weight water-soluble polymer of the low molecular weight blocked labeled lectin is dextran having the weight average molecular weight of less than 100,000.

6. The lectin-binding substance measurement method according to claim 1, wherein the high molecular weight water-soluble polymer and the low molecular weight water-soluble polymer are comprised of a same class of polymer.

7. The lectin-binding substance measurement method according to claim 1, wherein the first labeling substance, the second labeling substance, and the third labeling substance are a same labeling substance.

8. The lectin-binding substance measurement method according to claim 1, wherein the first lectin, the second lectin, and the third lectin are a same kind of lectin.

9. A blocked labeled lectin and a labeled lectin for use in the lectin-binding substance measurement method according to claim 1, wherein
the blocked labeled lectin is a combination of
a high molecular weight blocked labeled lectin including a first water-soluble carrier made of a high molecular weight water-soluble polymer having a weight average molecular weight of 200,000 or more, and a first labeling substance and a first lectin immobilized on the first water-soluble carrier and
a low molecular weight blocked labeled lectin including a second water-soluble carrier made of a low molecular weight water-soluble polymer having a weight average molecular weight of less than 100,000, and a second labeling substance and a second lectin immobilized on the second water-soluble carrier, the high molecular weight water-soluble polymer and the low molecular weight water soluble polymer are comprised of a same or different class of polymer, the labeled lectin comprises a third labeling substance and a third lectin, and excludes any water-soluble carrier, the first labeling substance, the second labeling substance and the third labeling substance are a same or different labeling substance, and the first lectin, the second lectin and the third lectin are a same or different kind of lectin.

10. A lectin-binding substance measurement kit for measuring a lectin-binding substance in a sample, comprising the blocked labeled lectin and the labeled lectin according to claim 9.

11. The lectin-binding substance measurement kit according to claim 10, wherein
the high molecular weight water-soluble polymer of the high molecular weight blocked labeled lectin is dextran having the weight average molecular weight of 200,000 or more, and the low molecular weight water-soluble polymer of the low molecular weight blocked labeled lectin is dextran having the weight average molecular weight of less than 100,000.

12. The lectin-binding substance measurement kit according to claim 10, further comprising a free water-soluble polymer.

13. The lectin-binding substance measurement kit according to claim 12, wherein the high molecular weight water-soluble polymer and the low molecular weight water-soluble polymer are comprised of a same class of polymer.

14. The lectin-binding substance measurement kit according to claim 13, wherein the free water-soluble polymer is the same class of polymer as the high molecular weight water soluble polymer and the low molecular weight water-soluble polymer.

15. The lectin-binding substance measurement kit according to claim 10, wherein the high molecular weight water-soluble polymer and the low molecular weight water-soluble polymer are comprised of a same class of polymer.

16. The lectin-binding substance measurement kit according to claim 10, wherein the first labeling substance, the second labeling substance, and the third labeling substance are a same labeling substance.

17. The lectin-binding substance measurement kit according to claim 10, wherein the first lectin, the second lectin and the third lectin are a same lectin.

\* \* \* \* \*